United States Patent
Brendel et al.

(10) Patent No.: US 6,903,216 B2
(45) Date of Patent: Jun. 7, 2005

(54) ANTHRANILAMIDES WITH HETEROARYLSULFONYL SIDE CHAIN, PROCESS OF PREPARATION, AND USE

(75) Inventors: Joachim Brendel, Bad Vilbel (DE); Thomas Böhme, Rüsselsheim (DE); Stefan Peukert, Frankfurt (DE); Heinz-Werner Kleemann, Bischofsheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 295 days.

(21) Appl. No.: 10/166,595

(22) Filed: Jun. 12, 2002

(65) Prior Publication Data

US 2003/0114499 A1 Jun. 19, 2003

(30) Foreign Application Priority Data

Jun. 12, 2001 (DE) .......................... 101 28 331

(51) Int. Cl.$^7$ ...................... C07D 215/36; A61K 31/47
(52) U.S. Cl. ...................... 546/172; 514/311; 514/312; 514/397; 514/445; 514/235; 514/380; 514/347; 546/153; 546/293; 548/312.1; 548/243; 544/405; 549/65
(58) Field of Search .................. 514/311, 312, 514/445, 397, 255, 380, 347; 546/172, 153, 293; 548/312.1, 243; 544/405; 549/65

(56) References Cited

U.S. PATENT DOCUMENTS 6,150,356 A    11/2000   Lloyd et al.
6,531,495 B1   3/2003    Brendel et al.

FOREIGN PATENT DOCUMENTS

| DE | 199 47 457 A1 | 4/2001 |
|---|---|---|
| EP | 0 686 625 A1 | 12/1995 |
| EP | 0 947 500 A1 | 10/1999 |
| WO | WO 96/25936 | 8/1996 |
| WO | WO 98/04521 | 2/1998 |
| WO | WO 98/18475 | 5/1998 |
| WO | WO 98/18476 | 5/1998 |
| WO | WO 00/02851 | 1/2000 |
| WO | WO 00/78145 A1 * | 12/2000 |

* cited by examiner

Primary Examiner—Shailendra Kumar
(74) Attorney, Agent, or Firm—Joseph D. Rossi

(57) ABSTRACT

This invention encompasses anthranilamides with heteroarylsulfonyl side chain, process for their preparation, their use as medicament or diagnostic aid, and pharmaceutical preparations containing them. Compounds of formula I,

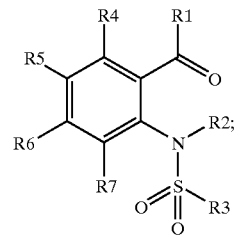

in which R1 to R7 have the meanings stated in the claims, act on the Kv1.5 potassium channel and inhibit a potassium current which is referred to as the ultra-rapidly activating delayed rectifier in the atrium of the human heart. They are therefore suitable as novel antiarrhythmic ingredients, such as for the treatment and prophylaxis of atrial arrhythmias, e.g. atrial fibrillation (AF) or atrial flutter.

20 Claims, No Drawings

ANTHRANILAMIDES WITH HETEROARYLSULFONYL SIDE CHAIN, PROCESS OF PREPARATION, AND USE

This application claims the priority of German application No. 10128331.8, filed on Jun. 12, 2001, under 35 U.S.C. 119, which is incorporated by reference.

DESCRIPTION

The invention relates to compounds of formula I, represented in the structure below, in which R1, R2, R3, R4, R5, R6 and R7 have the meanings as stated below, and to the use thereof, especially in pharmaceuticals.

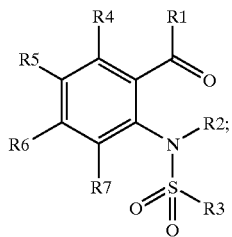

I

The present invention encompasses compounds of formula I wherein:

R1 is represented by the structures depicted below, in which, R1 is

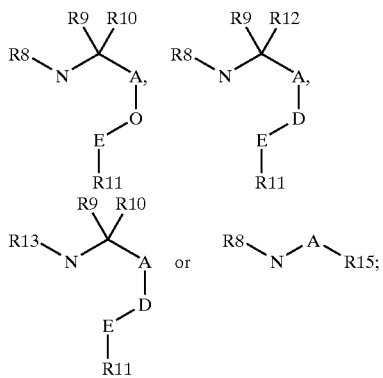

where A is —$C_nH_{2n}$— and n=0, 1, 2, 3, 4, or 5;
D is a bond or —O—;
E is —$C_mH_{2m}$— and m=0, 1, 2, 3, 4, or 5;
R8 is hydrogen, alkyl having 1, 2, 3, or 4 carbon atoms, or $C_pH_{2p}$—R14 where p=0, 1, 2, 3, 4, or 5 and where R14 is phenyl, naphthyl, or heteroaryl, where phenyl, naphthyl or heteroaryl are unsubstituted or substituted by 1, 2, or 3 substituents selected from F, Cl, Br, I, CF3, OCF3, NO2, CN, COOMe, CONH2, COMe, NH2, OH, alkyl having 1, 2, 3, or 4 carbon atoms, alkoxy having 1, 2, 3, or 4 carbon atoms, dimethylamino, sulfamoyl, methylsulfonyl and methylsulfonylamino;
R9 is hydrogen or alkyl having 1, 2, 3, 4, 5, or 6 carbon atoms;
R10 is hydrogen, alkyl having 1, 2, 3, or 4 carbon atoms, phenyl, naphthyl, or heteroaryl where phenyl, naphthyl, or heteroaryl are unsubstituted or substituted by 1, 2, or 3 substituents selected from F, Cl, Br, I, $CF_3$, $OCF_3$, $NO_2$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R11 is cycloalkyl having 3, 4, 5, or 6 carbon atoms, phenyl, naphthyl, thienyl, furyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl, where phenyl, naphthyl, thienyl, furyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1, 2, or 3 substituents selected from F, Cl, Br, I, $CF_3$, $OCF_3$, $NO_2$, CN, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R12 is alkyl having 1, 2, 3, or 4 carbon atoms, alkynyl having 1, 2, 3, or 4 carbon atoms, cycloalkyl having 3, 4, 5, or 6 carbon atoms, phenyl, naphthyl, or heteroaryl, where phenyl, naphthyl, or heteroaryl are unsubstituted or substituted by 1, 2, or 3 substituents selected from F, Cl, Br, I, $CF_3$, $OCF_3$, $NO_2$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R13 is $C_pH_{2p}$—R14 where p=0, 1, 2, 3, 4, or 5 and where R14 is phenyl, naphthyl, or heteroaryl, where phenyl, naphthyl, or heteroaryl are unsubstituted or substituted by 1, 2, or 3 substituents selected from F, Cl, Br, I, $CF_3$, $OCF_3$, $NO_2$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R15 is cycloalkyl having 3, 4, 5, 6, 7, or 8 carbon atoms;
R2 is hydrogen or alkyl having 1, 2, 3, or 4 carbon atoms;
R3 is heteroaryl where heteroaryl is unsubstituted or substituted by 1, 2, or 3 substituents selected from F, Cl, Br, I, CF3, OCF3, NO2, CN, COOMe, CONH2, COMe, NH2, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R4, R5, R6 and R7 are independently of one another, substituents selected from hydrogen, F, Cl, Br, I, $CF_3$, $OCF_3$, $NO_2$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
and the pharmaceutically acceptable salts thereof.

One embodiment of the invention includes compounds of formula I wherein:
R1 is represented by the structure below, in which, R1 is

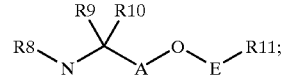

where A is —$C_nH_{2n}$— and n=0, 1, 2, or 3;
E is —$C_mH_{2m}$— and m=0, 1, 2, or 3;
R8 is hydrogen, alkyl having 1, 2, or 3 carbon atoms or $C_pH_{2p}$—R14 where p=0, 1, 2, or 3 and where R14 is phenyl, naphthyl or heteroaryl, where phenyl, naphthyl and heteroaryl are unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R9 is hydrogen or alkyl having 1, 2, 3, or 4 carbon atoms;

R10 is hydrogen, alkyl having 1, 2, or 3 carbon atoms, phenyl, naphthyl, or heteroaryl where phenyl, naphthyl, or heteroaryl are unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R11 is phenyl, naphthyl, thienyl, furyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, thienyl, furyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1, 2, or 3 substituents selected from F, Cl, CF$_3$, OCF$_3$, CN, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R2 is hydrogen or alkyl having 1, 2, or 3 carbon atoms;

R3 is heteroaryl, where heteroaryl is unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R4, R5, R6, and R7 are, independently of one another, substituents selected from hydrogen, F, Cl, CF$_3$, OCF$_3$, CN, COMe, OH, alkyl having 1, 2, 3, or 4 carbon atoms, methoxy, ethoxy, dimethylamino, sulfamoyl, methylsulfonyl, and methylsulfonylamino;

and the pharmaceutically acceptable salts thereof.

Another embodiment of the invention includes compounds of formula I wherein:

R1 is represented by the structure below in which, R1 is

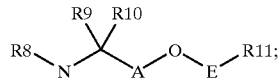

where A is —C$_n$H$_{2n}$— and n=0 or 1;
E is —C$_m$H$_{2m}$— and m=0 or 1;
R8 is hydrogen, alkyl having 1, 2, or 3 carbon atoms, or C$_p$H$_{2p}$—R14 where p=0 or 1 and where R14 is phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R9 is hydrogen, methyl, or ethyl;

R10 is hydrogen, alkyl having 1, 2, or 3 carbon atoms, phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl and, methylsulfonylamino;

R2 is hydrogen, methyl, or ethyl;

R3 is heteroaryl, where heteroaryl is unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R4, R5, R6, and R7 are, independently of one another, substituents selected from hydrogen, F, Cl, CF$_3$, OCF$_3$, CN, COMe, OH, alkyl having 1, 2, 3, or 4 carbon atoms, methoxy, ethoxy, dimethylamino, sulfamoyl, methylsulfonyl, and methylsulfonylamino;

and the pharmaceutically acceptable salts thereof.

An additional embodiment of the invention is drawn to compounds of formula I wherein:

R1 is represented by the structure below, in which R1 is

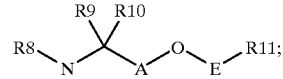

where A is —C$_n$H$_{2n}$— and n=0 or 1;
E is —C$_m$H$_{2m}$— and m=0 or 1;
R8 is hydrogen, alkyl having 1, 2, or 3 carbon atoms or C$_p$H$_{2p}$—R14 where p=0 or 1 and where R14 is phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, methyl, methoxy, ethoxy, dimethylamino, sulfamoyl, and methylsulfonyl;

R9 is hydrogen, methyl, or ethyl;

R10 is hydrogen, alkyl having 1, 2, or 3 carbon atoms, phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, methyl, methoxy, ethoxy, dimethylamino, sulfamoyl, and methylsulfonyl;

R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, CF$_3$, OCF$_3$, CN, COMe, methyl, methoxy, ethoxy, dimethylamino, sulfamoyl, and methylsulfonyl;

R2 is hydrogen;

R3 is heteroaryl, where heteroaryl is unsubstituted or substituted by 1 or 2 substituents selected from F, Cl, CF$_3$, OCF$_3$, CN, COMe, methyl, methoxy, ethoxy, dimethylamino, sulfamoyl, and methylsulfonyl;

R4 is hydrogen, F, Cl, CF$_3$, methyl, or methoxy;

R5 is hydrogen, F, Cl, CF$_3$, methyl, methoxy, COMe, OCF$_3$, CN, or OH;

R6 is hydrogen, F, Cl, CF$_3$, methyl, methoxy, or OH;

R7 is hydrogen, F, Cl, CF$_3$, methyl, ethyl, methoxy, or OH;

and the pharmaceutically acceptable salts thereof.

An optional embodiment of the invention is compounds of formula I wherein:

R1 is represented by the structure below in which R1 is

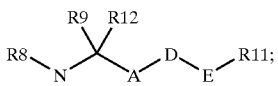

where A is —C$_n$H$_{2n}$— and n=0, 1, 2, or 3;
D is a bond or —O—;
E is —C$_m$H$_{2m}$— and m=0, 1, 2, or 3;
R8 is hydrogen, alkyl having 1, 2, or 3 carbon atoms, or C$_p$H$_{2p}$—R14 where p=0, 1, 2, or 3 and where R14 is phenyl, naphthyl, or heteroaryl, where phenyl, naphthyl, or heteroaryl are unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R9 is hydrogen or alkyl having 1, 2, 3, or 4 carbon atoms;
R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1, 2, or 3 substituents selected from F, Cl, CF$_3$, OCF$_3$, CN, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R12 is alkyl having 1, 2, or 3 carbon atoms, alkynyl having 1, 2, or 3 carbon atoms, cycloalkyl having 3, 4, 5, or 6 carbon atoms, phenyl, naphthyl, or heteroaryl, where phenyl, naphthyl, or heteroaryl are unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R2 is hydrogen or alkyl having 1, 2, or 3 carbon atoms;
R3 is heteroaryl, where heteroaryl is unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R4, R5, R6, and R7 are, independently of one another, substituents selected from hydrogen, F, Cl, CF$_3$, OCF$_3$, CN, COMe, OH, alkyl having 1, 2, 3, or 4 carbon atoms, methoxy, ethoxy, dimethylamino, sulfamoyl, methylsulfonyl, and methylsulfonylamino;

and the pharmacologically acceptable salts thereof.

Another embodiment of the invention is compounds of formula I wherein:

R1 is represented by the structure below in which R1 is

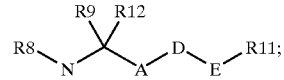

where A is —C$_n$H$_{2n}$— and n=0 or 1;
D is a bond or —O—;
E is —C$_m$H$_{2m}$— and m=0 or 1;
R8 is hydrogen, alkyl having 1, 2, or 3 carbon atoms, or C$_p$H$_{2p}$—R14 where p=0 or 1 and where R14 is phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;
R9 is hydrogen, methyl, or ethyl;
R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;
R12 is alkyl having 1, 2, or 3 carbon atoms, ethynyl, cyclopropyl, phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;
R2 is hydrogen, methyl, or ethyl;
R3 is heteroaryl, where heteroaryl is unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;
R4, R5, R6, and R7 are, independently of one another, substituents selected from hydrogen, F, Cl, CF$_3$, OCF$_3$, CN, COMe, OH, alkyl having 1, 2, 3, or 4 carbon atoms, methoxy, ethoxy, dimethylamino, sulfamoyl, methylsulfonyl, and methylsulfonylamino;

and the pharmacologically acceptable salts thereof.

Another embodiment of the invention is compounds of formula I wherein:

R1 is represented by the structure below in which R1 is

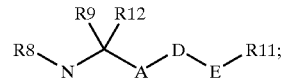

where A is —C$_n$H$_{2n}$— and n=0 or 1;
D is a bond or —O—;
E is —C$_m$H$_{2m}$— and m=0 or 1;

R8 is hydrogen, alkyl having 1, 2, or 3 carbon atoms, or $C_pH_{2p}$—R14 where p=0 or 1 and where R14 is phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, methyl, methoxy, ethoxy, dimethylamino, sulfamoyl, methylsulfonyl, and methylsulfonylamino;

R9 is hydrogen, ethyl, or methyl;

R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, $CF_3$, $OCF_3$, CN, COMe, methyl, methoxy, ethoxy, dimethylamino, sulfamoyl, and methylsulfonyl;

R12 is alkyl having 1, 2, or 3 carbon atoms, ethynyl, cyclopropyl, phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, methyl, methoxy, ethoxy, dimethylamino, sulfamoyl, methylsulfonyl, and methylsulfonylamino;

R2 is hydrogen;

R3 is heteroaryl, where heteroaryl is unsubstituted or substituted by 1 or 2 substituents selected from F, Cl, $CF_3$, $OCF_3$, CN, COMe, methyl, methoxy, ethoxy, dimethylamino, sulfamoyl, and methylsulfonyl;

R4 is hydrogen, F, Cl, $CF_3$, methyl, or methoxy;

R5 is hydrogen, F, Cl, $CF_3$, methyl, methoxy, COMe, $OCF_3$, CN, or OH;

R6 is hydrogen, F, Cl, $CF_3$, methyl or methoxy, or OH;

R7 is hydrogen, F, Cl, $CF_3$, methyl, ethyl, methoxy, or OH;

and the pharmacologically acceptable salts thereof.

Another embodiment of the invention is compounds of formula I wherein:

R1 is represented by the structure below in which R1 is

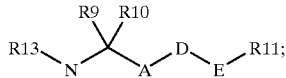

where A is —$C_nH_{2n}$— and n=0, 1, 2, or 3;
D is a bond or —O—;
E is —$C_mH_{2m}$— and m=0, 1, 2, or 3;
R9 is hydrogen or alkyl having 1, 2, 3, or 4 carbon atoms;
R10 is hydrogen, alkyl having 1, 2, or 3 carbon atoms, phenyl, naphthyl, or heteroaryl where phenyl, naphthyl, or heteroaryl are unsubstituted or substituted by 1, 2, or 3 substituents selected from F, Cl, $CF_3$, $OCF_3$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R11 is phenyl, naphthyl, thienyl, furanyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, thienyl, furanyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1, 2, or 3 substituents selected from F, Cl, $CF_3$, $OCF_3$, CN, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R13 is $C_pH_{2p}$—R14 where p=0, 1, 2, or 3 and where R14 is phenyl, naphthyl, or heteroaryl, where phenyl, naphthyl, and heteroaryl are unsubstituted or substituted by 1, 2, or 3 substituents selected from F, Cl, $CF_3$, $OCF_3$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R2 is hydrogen or alkyl having 1, 2, or 3 carbon atoms;

R3 is heteroaryl, where heteroaryl is unsubstituted or substituted by 1, 2, or 3 substituents selected from F, Cl, $CF_3$, $OCF_3$, CN, COOMe, $CONH_2$, COMe, $NH_2$, OH, alkyl having 1, 2 3, or 4 carbon atoms, alkoxy having 1, 2, 3, or 4 carbon atoms, dimethylamino, sulfamoyl, methylsulfonyl, and methylsulfonylamino;

R4, R5, R6 and R7 are, independently of one another, substituents selected from hydrogen, F, Cl, $CF_3$, $OCF_3$, CN, COMe, OH, alkyl having 1, 2, 3, or 4 carbon atoms, methoxy, ethoxy, dimethylamino, sulfamoyl, methylsulfonyl, and methylsulfonylamino;

and the pharmaceutically acceptable salts thereof.

An optional embodiment of the invention is compounds of formula I wherein:

R1 is represented by the structure below in which R1 is

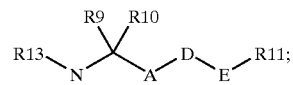

where A is —$C_nH_{2n}$— and n=0 or 1;
D is a bond or —O—;
E is —$C_mH_{2m}$— and m=0 or 1;
R9 is hydrogen, methyl, or ethyl;
R10 is hydrogen, alkyl having 1, 2, or 3 carbon atoms, phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, alkyl having 1, 2, 3, or 4 carbon atoms, methoxy, ethoxy, dimethylamino, sulfamoyl, methylsulfonyl, and methylsulfonylamino;
R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, $CF_3$, $OCF_3$, CN, COMe, alkyl having 1, 2, 3, or 4 carbon atoms, methoxy, ethoxy, dimethylamino, sulfamoyl, methylsulfonyl, and methylsulfonylamino;
R13 is $C_pH_{2p}$—R14 where p=0 or 1 and where R14 is phenyl, naphthyl, or heteroaryl, where phenyl, naphthyl, or heteroaryl are unsubstituted or substituted by 1 or 2 substituents selected from F, Cl, $CF_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R2 is hydrogen, methyl, or ethyl;

R3 is heteroaryl, where heteroaryl is unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R4, R5, R6, and R7 are, independently of one another, substituents selected from hydrogen, F, Cl, CF$_3$, OCF$_3$, CN, COMe, OH, alkyl having 1, 2, 3, or 4 carbon atoms, methoxy, ethoxy, dimethylamino, sulfamoyl, methylsulfonyl, and methylsulfonylamino;

and the pharmaceutically acceptable salts thereof.

An optional embodiment of the invention is compounds of formula I wherein:

R1 is represented by the structure below in which R1 is

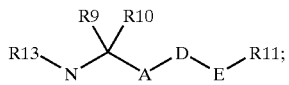

where A is —C$_n$H$_{2n}$ and n=0 or 1;

D is a bond or —O—;

E is —C$_m$H$_{2m}$— and m=0 or 1;

R9 is hydrogen, ethyl, or methyl;

R10 is hydrogen, alkyl having 1, 2, or 3 carbon atoms, phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, methyl, methoxy, ethoxy, dimethylamino, sulfamoyl, and methylsulfonyl;

R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, CF$_3$, OCF$_3$, CN, COMe, methyl, methoxy, ethoxy, dimethylamino, sulfamoyl, and methylsulfonyl;

R13 is C$_p$H2$_p$—R14 where p=0 or 1 and where R14 is phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, methyl, methoxy, ethoxy, dimethylamino, sulfamoyl, and methylsulfonyl;

R2 is hydrogen;

R3 is heteroaryl, where heteroaryl is unsubstituted or substituted by 1 or 2 substituents selected from F, Cl, CF$_3$, OCF$_3$, CN, COMe, methyl, methoxy, ethoxy, dimethylamino, sulfamoyl, and methylsulfonyl;

R4 is hydrogen, F, Cl, CF$_3$, methyl, or methoxy;

R5 is hydrogen, F, Cl, CF$_3$, methyl, methoxy, COMe, OCF$_3$, CN, or OH;

R6 is hydrogen, F, Cl, CF$_3$, methyl, methoxy, or OH;

R7 is hydrogen, F, Cl, CF$_3$, methyl, ethyl, methoxy, or OH;

and the pharmaceutically acceptable salts thereof.

An alternative embodiment of the invention is compounds of formula I wherein:

R1 is represented by the structure below in which

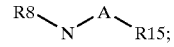

where A is —C$_n$H$_{2n}$— where n=0, 1, 2, or 3;

R8 is hydrogen, alkyl having 1, 2, or 3 carbon atoms, or C$_p$H$_{2p}$—R14 where p=0, 1, 2, or 3 and where R14 is phenyl, naphthyl, or heteroaryl, where phenyl, naphthyl, or heteroaryl are unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R15 is cycloalkyl having 3, 4, 5, 6, or 7 carbon atoms;

R2 is hydrogen or alkyl having 1, 2, or 3 carbon atoms;

R3 is heteroaryl, where heteroaryl is unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R4, R5, R6, and R7 are, independently of one another, substituents selected from hydrogen, F, Cl, CF$_3$, OCF$_3$, CN, COMe, OH, alkyl having 1, 2, 3, or 4 carbon atoms, methoxy, ethoxy, dimethylamino, sulfamoyl, methylsulfonyl, and methylsulfonylamino;

and the pharmaceutically acceptable salts thereof.

An additional embodiment of the invention is compounds of formula I wherein:

R1 is represented by the structure below in which R1 is

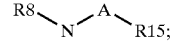

where A is —C$_n$H$_{2n}$— and n=0 or 1;

R8 is hydrogen, alkyl having 1, 2, or 3 carbon atoms, or C$_p$H$_{2p}$—R14 where p=0 or 1 and where R14 is phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R15 is cycloalkyl having 3, 4, 5, 6, or 7 carbon atoms;

R2 is hydrogen, methyl, or ethyl;

R3 is heteroaryl, where heteroaryl is unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R4, R5, R6, and R7 are, independently of one another, substituents selected from hydrogen, F, Cl, CF$_3$, OCF$_3$, CN, COMe, OH, alkyl having 1, 2, 3, or 4 carbon atoms, methoxy, ethoxy, dimethylamino, sulfamoyl, methylsulfonyl, and methylsulfonylamino;

and the pharmaceutically acceptable salts thereof.

Another optional embodiment of the invention is compounds of formula I wherein:

R1 is represented by the structure below in which R1 is

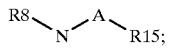

where A is —$C_nH_{2n}$— and n=0 or 1;

R8 is hydrogen, alkyl having 1, 2, or 3 carbon atoms, or $C_pH_{2p}$—R14 where p=0 or 1 and where R14 is phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, methyl, methoxy, ethoxy, dimethylamino, sulfamoyl, and methylsulfonyl;

R15 is cycloalkyl having 3, 4, 5, 6, or 7 carbon atoms;

R2 is hydrogen;

R3 is heteroaryl, where heteroaryl is unsubstituted or substituted by 1 or 2 substituents selected from F, Cl, $CF_3$, $OCF_3$, CN, COMe, methyl, methoxy, ethoxy, dimethylamino, sulfamoyl, and methylsulfonyl;

R4 is hydrogen, F, Cl, $CF_3$, methyl, or methoxy;

R5 is hydrogen, F, Cl, $CF_3$, methyl, methoxy, COMe, $OCF_3$, CN, or OH;

R6 is hydrogen, F, Cl, $CF_3$, methyl, methoxy, or OH;

R7 is hydrogen, F, Cl, $CF_3$, methyl, ethyl, methoxy, or OH;

and the pharmaceutically acceptable salts thereof.

As described in this disclosure, heteroaryl means radicals which are derived from phenyl or naphthyl and in which one or more CH groups are replaced by N and/or in which at least two adjacent CH groups are replaced by S, NH or O (to form a five-membered aromatic ring, for example). It is also possible for one or both atoms at the site of fusion of bicyclic radicals (as in indolizinyl, for instance,) to be nitrogen atoms. Heteroaryl also means furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl.

Alkyl radicals and alkylene radicals may be straight-chain or branched. This also applies to the alkylene radicals of the formula $C_mH_{2m}$, $C_nH_{2n}$, and $C_pH_{2p}$. Alkyl radicals and alkylene radicals may also be straight-chain or branched if they are substituted or present in other radicals, e.g. in an alkoxy radical or in a fluorinated alkyl radical. Examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, and eicosyl. The divalent radicals derived from these radicals, e.g. methylene, 1,1-ethylene, 1,2-ethylene, 1,1-propylene, 1,2-propylene, 2,2-propylene, 1,3-propylene, 1,1-butylene, 1,4-butylene, 1,5-pentylene, 2,2-dimethyl-1,3-propylene, 1,6-hexylene, etc., are examples of alkylene radicals.

If the compounds of formula I contain one or more acidic or basic groups or one or more basic or acidic heterocycles, the invention also includes the corresponding physiologically or toxicologically acceptable salts, in particular the pharmaceutically utilizable salts. Thus, the compounds of formula I which have acidic groups, e.g. one or more COOH groups, can be used, for example, as alkali metal salts, such as sodium or potassium salts, or as alkaline earth metal salts, e.g. calcium or magnesium salts, or as ammonium salts, e.g. as salts with ammonia or organic amines or amino acids. Compounds of formula I which have one or more basic, i.e. protonatable, groups or contain one or more basic heterocyclic rings, can also be used in the form of their physiologically tolerated acid addition salts with inorganic or organic acids, for example as hydrochlorides, phosphates, sulfates, methanesulfonates, acetates, lactates, maleates, fumarates, malates, and gluconates, etc. If the compounds of formula I contain both acidic and basic groups in the molecule, the invention includes not only the salt forms described but also inner salts, called betaines. As described herein, the term "pharmaceutically acceptable salts" is intended to cover all salt forms, as mentioned above for example, that are pharmaceutically acceptable. Salts can be obtained from the compounds of formula I by conventional processes, for example by combining with an acid or base in a solvent or dispersant or else by anion exchange from other salts.

The compounds of formula I may, when appropriately substituted, exist in stereoisomeric forms. If the compounds of formula I contain one or more centers of asymmetry, these may have, independently of one another, the S configuration or the R configuration. The invention includes all possible stereoisomers, e.g. enantiomers or diastereomers, and mixtures of two or more stereoisomeric forms, e.g. enantiomers and/or diastereomers, in any ratios. The invention thus includes, for example, enantiomers in enantiopure form, both as levorotatory and as dextrorotatory antipodes, and in the form of mixtures of the two enantiomers in various ratios or in the form of racemates. Individual stereoisomers can be prepared if required by fractionating a mixture by conventional methods or, for example, by stereoselective synthesis. If mobile hydrogen atoms are present, all tautomeric forms of the compounds of formula I are also encompassed by the present invention.

The compounds of formula I disclosed herein and/or their pharmaceutically acceptable salts can be mixed together with one or more solid or liquid pharmaceutical carriers and/or excipients and, if desired, with other active pharmaceutical ingredients, into a suitable administration form or dosage form. This dosage form may then be used as a pharmaceutical in human medicine or veterinary medicine. Pharmaceuticals which comprise compounds of formula I disclosed herein and/or their pharmaceutically acceptable salts can be administered orally, parenterally, intravenously, rectally, by inhalation or topically. The optimal administration will depend on the individual case, e.g., the particular manifestation of the disease to be treated. Suitable pharmaceutically acceptable excipients are familiar to the skilled worker. Such excipients include solvents, gel formers, suppository bases, tablet excipients and other active ingredient carriers, for example, antioxidants, dispersants, emulsifiers, antifoams, flavor corrigents, preservatives, solubilizers, agents to achieve a depot effect, buffer substances or colorants.

For oral use, the active compounds are mixed with additives suitable for this purpose, such as carriers, stabilizers or inert diluents, and converted by conventional methods into the suitable administration forms such as tablets, coated tablets, hard gelatin capsules, aqueous, alcoholic or oily solutions. Examples of inert carriers which can be used include gum arabic, magnesia, magnesium carbonate, potassium phosphate, lactose, glucose or starch, especially corn starch. Preparation is possible in this connection both as dry and as wet granules. Suitable oily carriers or solvents include, for example, vegetable or animal oils, such as sunflower oil or fish liver oil. Examples of suitable solvents for aqueous or alcoholic solutions include water, ethanol or sugar solutions or mixtures thereof. Further examples of excipients, also for other administration forms, are polyethylene glycols and polypropylene glycols. For subcutaneous or intravenous administration, the active compounds are converted into a solution, suspension or emulsion, if desired, with the substances customary for this purpose such as solubilizers, emulsifiers or other excipients. The compounds of formula I and their pharmaceutically acceptable salts can also be lyophilized and the resulting lyophilizates used, for example, to produce products for injection or infusion. Examples of suitable solvents include water, physiological saline or alcohols, e.g., ethanol, propanol, glycerol, as well as sugar solutions such as glucose or mannitol solutions, and mixtures of the various solvents mentioned. Suitable pharmaceutical formulations for administration in the form of aerosols or sprays include, for example, solutions, suspensions or emulsions of the active ingredients of formula I, or their pharmaceutically acceptable salts, in a pharmaceutically acceptable solvent such as ethanol or water, or a mixture of such solvents. The formulation can, if required, also contain other pharmaceutical excipients such as surfactants, emulsifiers and stabilizers, and a propellant gas.

Without limiting other possible biological mechanisms of action encompassed by the present invention, it is envisioned that the compounds of the present invention of formula I act on the so-called Kv1.5 potassium channel to inhibit a potassium current, also referred to as ultra-rapidly activating delayed rectifier, in the atrium of the human heart. The compounds are therefore suitable as novel antiarrhythmic active ingredients, in particular for the treatment and prophylaxis of atrial arrhythmias, e.g. atrial fibrillation (AF) or atrial flutter.

Atrial fibrillation (AF) and atrial flutter are the most common persistent form of cardiac arrhythmias. The occurrence increases with increasing age and frequently leads to fatal sequelae such as, for example, stroke. It affects about 1 million Americans each year and leads to more than 80,000 strokes annually in the USA. The class I and III antiarrhythmics in use at present reduce the rate of recurrence of AF but are used to only a limited extent because of their potential proarrhythmic side effects. There is thus a great medical need to develop better medicaments for the treatment of atrial arrhythmias (S. Nattel, Am. Heart J. 130, 1995, 1094–1106; "Newer developments in the management of atrial fibrillation").

It has been shown that most supraventricular arrhythmias are subject to so-called reentry waves. Such reentries occur when the cardiac tissue has a slow conductivity and, at the same time, very short refractory periods. Increasing the myocardial refractory period by prolonging the action potential is an acknowledged mechanism for terminating arrhythmias and preventing development thereof (T. J. Colatsky et al., Drug Dev. Res. 19, 1990, 129–140; "Potassium channels as targets for antiarrhythmic drug action"). The length of the action potential is essentially determined by the extent of repolarizing K$^+$ currents which flow out of the cell through various K$^+$ channels. Particularly great importance is ascribed in this connection to a so-called delayed rectifier $I_K$ which consists of 3 different components: $IK_r$, $IK_s$, and $IK_{ur}$.

Most of the known class III antiarrhythmics (e.g. dofetilide, E4031, and d-sotalol) block predominantly or exclusively the rapidly activating potassium channel, $IK_r$, which can be detected both in cells of the human ventricle and in the atrium. However, it has emerged that these compounds have an increased proarrhythmic risk at heart rates which are low or normal, and arrhythmias referred to as torsades de pointes have been observed in particular (D. M. Roden, Am. J. Cardiol. 72, 1993, 44B–49B; "Current status of class III antiarrhythmic drug therapy"). Besides this high risk, which is fatal in some cases, when the rate is low, the activity of the $I_{Kr}$ blockers has been found to decline under the conditions of tachycardia, which is just where the effect is required ("negative use-dependence"). Whereas some of these disadvantages can possibly be overcome by blockers of the slowly activating component ($IK_s$), their efficacy has not yet been proven because no clinical investigations with $IK_s$ channel blockers are known.

The "particularly rapidly" activating and very slowly inactivating component of the delayed rectifier $IK_{ur}$ (=ultra-rapidly activating delayed rectifier), which corresponds to the Kv1.5 channel, plays a particularly large part in the repolarization time in the human atrium. Inhibition of the $IK_{ur}$ potassium outward current thus represents, by comparison with inhibition of $IK_r$ or $IK_s$, a particularly effective method for prolonging the atrial action potential and thus for terminating or preventing atrial arrhythmias. Mathematical models of the human action potential suggest that the beneficial effect of blockade of the $IK_{ur}$ ought to be particularly pronounced precisely under the pathological conditions of chronic atrial fibrillation (M. Courtemanche, R. J. Ramirez, S. Nattel, Cardiovascular Research 1999, 42, 477–489: "Ionic targets for drug therapy and atrial fibrillation-induced electrical remodeling: insights from a mathematical model").

In contrast to $IK_r$ and $IK_s$, which also occur in the human ventricle, although $IK_{ur}$ plays a significant part in the human atrium it does not in the ventricle. For this reason, when the $IK_{ur}$ current is inhibited, in contrast to blockade of $IK_r$ or $IK_s$, the risk of a proarrhythmic effect on the ventricle is precluded from the outset. (Z. Wang et al., Circ. Res. 73, 1993, 1061–1076: "Sustained Depolarisation-Induced Outward Current in Human Atrial Myocytes"; G.-R. Li et al., Circ. Res. 78, 1996, 689–696: "Evidence for Two Components of Delayed Rectifier K$^+$-Current in Human Ventricular Myocytes"; G. J. Amos et al., J. Physiol. 491, 1996, 31–50: "Differences between outward currents of human atrial and subepicardial ventricular myocytes").

Antiarrhythmics which act via selective blockade of the $IK_{ur}$ current or Kv1.5 channel have not to date been available on the market. Although numerous active pharmaceutical ingredients (e.g. tedisamil, bupivacaine, or sertindole) have been described to have a blocking effect on the Kv1.5 channel, in each of these cases the Kv1.5 blockade is only a side effect in addition to other principal effects of the substances.

Aminoindanes are described as potassium channel blockers which block the Kv1.5 channel in WO 98 04 521. The use of various pyridazinones and phosphine oxides as antiarrhythmics which are said to act via $IK_{ur}$ blockade is described in applications WO 98 18 475 and WO 98 18 476. Said compounds were also described as immunosuppressants in WO 96 25 936. It is important to note that all the compounds described in the above mentioned applications have structures which are completely different from the compounds disclosed in this present application. It has now been found, surprisingly and unexpectedly, that the compounds disclosed in this invention, heteroarylsulfonylanthranilamides, are potent blockers of the human Kv1.5 channel. They can therefore be used as novel antiarrhythmics with a particularly advantageous safety profile. The compounds are suitable for treating supraventricular arrhythmias, e.g. atrial fibrillation or atrial flutter.

The compounds of formula I can also be combined with other active pharmaceutical ingredients to achieve an advantageous therapeutic effect. Thus, in the treatment of cardiovascular disorders, combinations with substances acting on the cardiovascular system are possible and advantageous. Suitable combination partners of this type include, for example, class I, class II or class III antiarrhythmic agents, such as $IK_s$- or $IK_r$ channel blockers (e.g., dofetilide); antihypertensive substances, such as ACE inhibitors (e.g., enalapril, captopril, ramipril); angiotensin antagonists; $K^+$ channel activators; alpha- and beta-receptor blockers; sympathomimetic and adrenergic compounds; $Na^+/H^+$ exchange inhibitors; calcium channel antagonists; phosphodiesterase inhibitors; and other positively inotropic substances, such as digitalis glycosides or diuretics. The compounds of the invention have not previously been disclosed. Some structurally related compounds are described in WO 0002851, EP 0 686 625 A1 and EP 0 947 500 A1. However, no potassium channel-blocking activity is disclosed for the anthranilic acid derivatives described therein.

DETAILED DESCRIPTION OF THE INVENTION

Compounds of the present invention can be prepared, for example, as shown in scheme 1 by initially reacting an amino carboxylic acid of the formula VI in a solvent such as water, pyridine or an ether in the presence of a base with a sulfonyl chloride of the formula $R3—SO_2—Cl$ or with a sulfonic anhydride. Suitable bases are inorganic bases such as, for example, sodium carbonate or organic bases such as, for example, pyridine or triethylamine. The resulting sulfonylamino carboxylic acid of the formula VII can then be activated, for example, by reaction with a chlorinating agent such as, for example, phosphorus pentachloride, phosphorus oxychloride or thionyl chloride, in an inert solvent to give an acid chloride of formula VIII and then be reacted with an amine H—R1 to give the title compounds of formula I. However, activation of the carboxyl group in the compound of formula VII can also take place in a different way, for example, by one of the numerous methods familiar to the ordinary skilled artisan and used in peptide chemistry for forming amide bonds, for example, by conversion into a mixed anhydride or an activated ester or with use of a carbodiimide such as dicyclohexylcarbodiimide.

Reaction of the activated sulfonylamino carboxylic acid with an amine H—R1 can be advantageously carried out in an inert solvent such as, for example, pyridine, tetrahydrofuran or toluene without addition or with addition of an inert base, for example, a tertiary amine or pyridine.

Scheme 1

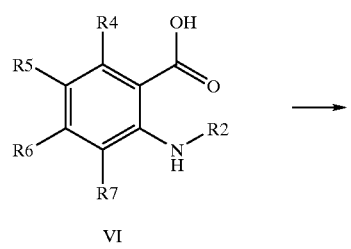

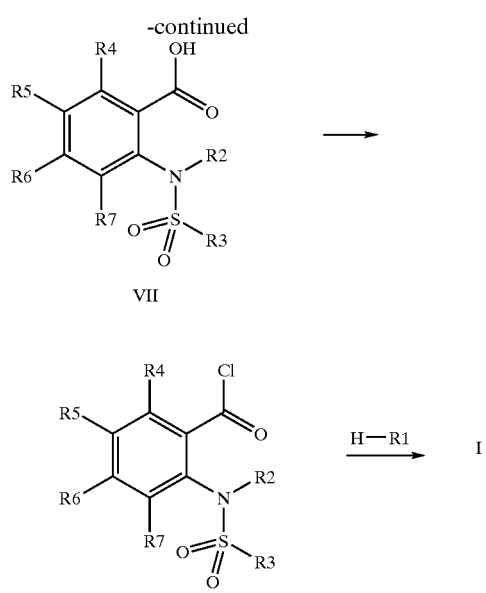

Abbreviations described herein have the following meaning:

| | |
|---|---|
| BuLi | Butyllithium |
| CDI | Carbonyldiimidazole |
| DIC | Diisopropylcarbodiimide |
| DIP | Diisopropyl ether |
| DIPEA | Diisopropylethylamine |
| DMAP | 4-Dimethylaminopyridine |
| DMF | N,N-Dimethylformamide |
| EA | Ethyl acetate |
| EDAC | N-Ethyl-N'-(3-dimethylaminopropyl)-carbodiimide hydrochloride |
| ES | Electrospray mass spectrometric data |
| HOBT | 1-Hydroxy-1H-benzotriazole |
| Me | Methyl |
| M.p. | Melting point (unless otherwise indicated, the melting points of the unpurified crude products are stated; the melting points of the respective pure substances may very well be distinctly higher) |
| MS | mass spectrometric data |
| MTB | t-Butyl methyl ether |
| Rf | Ratio to front |
| RT | Room temperature |
| THF | Tetrahydrofuran |
| TOTU | O-[(Cyano(ethoxycarbonyl)methylene)amino]-1,1,3,3-tetramethyluronium tetrafluoroborate |

General Method 1: Reaction of Anthranilic Acids with Sulfonyl Chlorides to Give O-sulfonylaminobenzoic Acids (Analogous to *Organic Syntheses* 1952, 32, 8).

1.2 mol of the appropriate sulfonyl chloride were added in portions to a solution of 260 g (2.4 mol) of sodium carbonate and 1 mol of the appropriate anthranilic acid in 1.5 of water at 60° C. The reaction mixture was heated at 60–80° C. until reaction is complete (about 1–6 h), adding further sulfonyl chloride if necessary. After cooling, the reaction mixture was poured into 500 ml of 6 mol hydrochloric acid, and the precipitate was filtered off with suction and dried in an oven at 45° C. in vacuo. If the product did not result as crystals, it was isolated by extraction with ethyl acetate.

Precursor 1 a: 4-Fluoro-2-(quinoline-8-sulfonylamino)benzoic acid

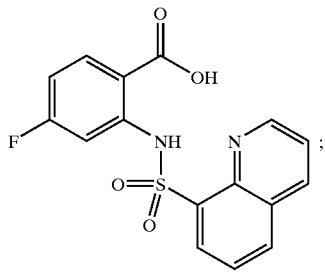

7.6 g of the title compound were obtained as a white solid by general method 1 from 5.0 g of 2-amino-4-fluorobenzoic acid and 8.8 g of 8-quinolinesulfonyl chloride. M.p.: 248° C.; MS (ES): 347 (M+1).

Precursor 1 b: 6-Chloro-2-(quinoline-8-sulfonylamino)benzoic acid

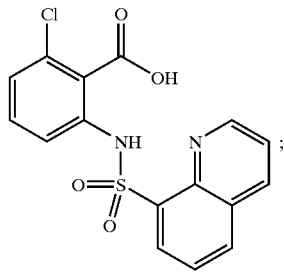

8.3 g of the title compound were obtained as a solid by general method 1 from 5.0 g of 2-amino-6-chlorobenzoic acid and 8.0 g of 8-quinolinesulfonyl chloride. M.p.: 88° C.; MS (ES): 363 (M+1).

Precursor 1 c: 3-Chloro-2-(quinoline-8-sulfonylamino)benzoic acid

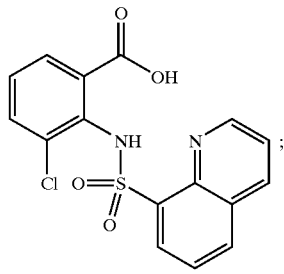

4.1 g of the title compound were obtained by general method 1 from 5.0 g of 2-amino-6-chlorobenzoic acid and 8.0 g of 8-quinolinesulfonyl chloride. MS (ES): 363 (M+1).

The following other precursors were synthesized inter alia by the general method described herein by General Method 1:

| Precursor | Structure | Mass (ES) |
|---|---|---|
| 1d | 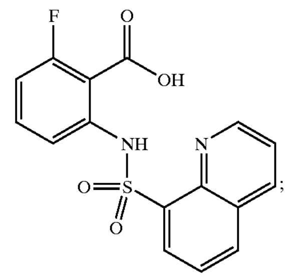 | 347 (M + 1) |
| 1e | 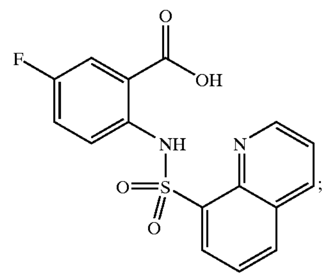 | 347 (M + 1) |
| 1f | 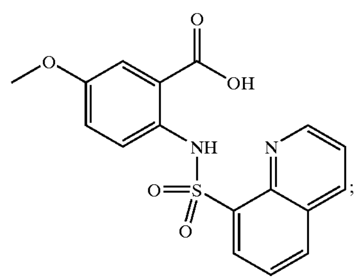 | 359 (M + 1) |

General Method 2: Conversion of Sulfonylaminobenzoic Acids into the Corresponding Acid Chlorides:

(A) with phosphorus pentachloride. 8 mmol of the sulfonylaminobenzoic acid were suspended in 15 ml of dry toluene and, at room temperature, 9.6 mmol of phosphorus pentachloride was slowly introduced. The mixture was stirred at 50° C. for 3 h and, after cooling to 0°C., the acid chloride was filtered off with suction, washed with a little toluene and dried in a vacuum oven at 45° C.

(B) with thionyl chloride. 8 mmol of the sulfonylaminobenzoic acid was heated in 6 ml of thionyl chloride at 60° C. for 3 h and, after concentration, the residue is coevaporated twice with toluene.

General Method 3A: Preparation of Secondary Amines by Reductive Amination 0.18 mmol of primary amine was dissolved in 200 ml of methanol and, after addition of 0.09 mol of aldehyde, 0.18 mmol of sodium cyanoborohydride and 0.18 mmol of glacial acetic acid, was stirred at room temperature for 6 h. The solution was concentrated, taken up in ethyl acetate and washed twice with $NaHCO_3$ solution. The organic phase was concentrated and the residue was distilled off under high vacuum. In the case of secondary amines of low volatility, volatile constituents were distilled out and the residue was dissolved in ether/THF and, after addition of an ethereal HCl solution, the precipitated hydrochloride was filtered off with suction, washed with ether and dried. The prepared secondary amines were employed without further purification for the reactions with the sulfonylaminobenzoyl chlorides or sulfonylaminobenzoic acids.

Precursor 3 a: Benzyl-(1-methyl-1H-imidazol-2-ylmethyl)-amine

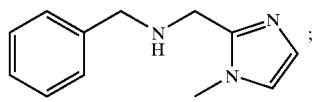

The hydrochloride (20.5 g) was prepared by general method 3 A from 19.4 g of benzylamine and 10 g of 2-formyl-1-methylimidazole. MS (ES+): m/z=202 (M+1).

Precursor 3 b: Benzyl-pyridin-3-ylmethylamine

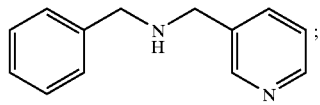

The secondary amine (2.8 g) was prepared by general method 3 A from 4.32 g of 3-pyridylmethylamine and 2.12 g of benzaldehyde after Kugelrohr distillation at 0.1 mbar and 130° C. MS (ES+): m/z=199 (M+1).

Precursor 3 c: Benzyl-(3-imidazol-1-yl-propyl)-amine

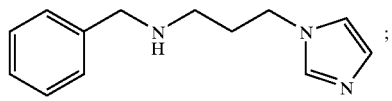

The secondary amine (3.5 g) was prepared by general method 3 A from 12.5 g of 3-imidazol-1-yl-propylamine and 5.3 g of benzaldehyde after Kugelrohr distillation at 0.1 mbar and 130° C. MS (ES+): m/z=216 (M+1).

The following other precursors were prepared inter alia by general method 3 A:

| Precursor | Structure | Mass |
|---|---|---|
| 3d | 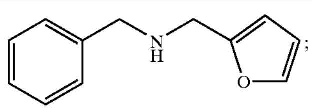 | 188 (M + 1) |
| 3e | 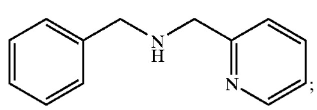 | 199 (M + 1) |
| 3f | 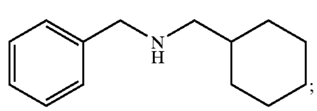 | 204 (M + 1) |
| 3g | 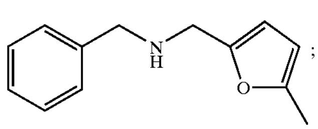 | 202 (M + 1) |
| 3h | 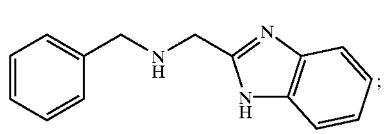 | 238 (M + 1) |
| 3i | | 162 (M + 1) |
| 3j | | 163 (M + 1) |
| 3k | | 177 (M + 1) |

General Method 3B: Preparation of α-branched Amines from Ketones.

A solution of 67 mmol of the appropriate ketone in 120 ml of ethanol was added dropwise to a solution of 200 mmol of hydroxylammonium chloride and 200 ml of sodium acetate in 120 ml of water at 30° C., and the mixture was heated at 60° C. until reaction is complete (1–3 h). After cooling, the reaction mixture was diluted with water, and the precipitated oxime was filtered off with suction or, if necessary, isolated by extraction. The resulting product was dissolved in 100 ml of methanol, 100 ml of THF and 10 ml of concentrated ammonia solution and hydrogenated in the presence of Raney nickel at RT and atmospheric pressure until hydrogen uptake ceases. Removal of the catalyst by filtration and concentration of the reaction mixture resulted in the corresponding amine which was purified by chromatography if necessary.

Precursor 3 I: 1-Benzylpropylamine

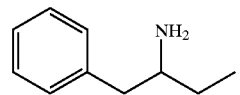

4.5 g of the title compound were obtained by general method 3 B from 10 g of 1-phenyl-2-butanone.

Precursor 3 m: 1-Pyridin-4-yl-propylamine

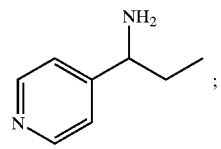

10.2 g of the title compound were obtained by general method 3 B from 10 g of 4-propionylpyridine.

Precursor 3 n: 1-Pyridin-3-yl-propylamine

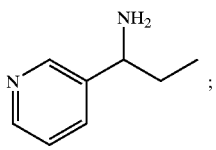

0.9 g of the title compound was obtained by general method 3 B from 1 g of 1-pyridin-3-yl-propane-1-one Precursor 3o: 1-Cyclopropyl-1-phenylmethylamine hydrochloride

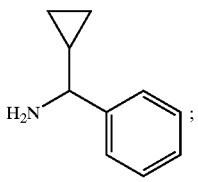

a) N-(Cyclopropylphenylmethyl)-formamide: 14.8 g (0.1 mol) of cyclopropyl phenyl ketone, 11.4 ml (0.3 mol) of formic acid and 20 ml (0.5 mol) of formamide were heated at 160° C. for 18 h. Cooling and addition of 100 ml of water were followed by extraction 2× with 50 ml of ether each time. The ethereal phase was washed with 50 ml of 10% $Na_2CO_3$ solution, dried over $Na_2SO_4$ and concentrated. 13.6 g (77.4 mmol) of a yellow oil were obtained.

b) 1-Cyclopropyl-1-phenylmethylamine hydrochloride: 13.6 g (77.4 mmol) of N-(cyclopropylphenylmethyl)-formamide (see a) were heated to reflux in 100 ml of 2N HCl for 18 h. After cooling and extraction 2× with 50 ml of dichloromethane each time, the aqueous phase was concentrated. The residue was taken up in 30 ml of 2-propanol, heated to boiling and cooled in a refrigerator overnight. The crystals of 1-cyclopropyl-1-phenylmethylamine hydrochloride (3.85 g, 21 mmol) which had separated out were filtered off with suction and dried in a vacuum oven.

Precursor 3p: Cyclopropylpyridin-2-yl-methylamine hydrochloride

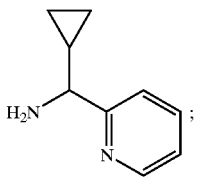

a) Cyclopropylpyridin-2-yl-methyleneamine: 25 g (157.5 mmol) of 2-bromopyridine in 100 ml of diethyl ether were added dropwise over the course of 20 min to 100 ml (160 mmol) of n-BuLi solution in 300 ml of diethyl ether at −70° C. The dark red solution was stirred for 5 h and then 8.8 g (131 mmol) of cyclopropanecarbonitrile in 100 ml of ether were added. The mixture was stirred at −70° C. for 30 min, warmed to room temperature and stirred for a further 30 min. Then 15 g of $Na_2SO_4 \times 10\ H_2O$ were added and stirring was continued for 1 h. Addition of $Na_2SO_4$ to the red solution was followed by filtration and concentration. The product was distilled in a Kugelrohr apparatus at 75° C.–120° C./0.3 mbar as a pale yellow oil (18.6 g, 127 mmol) and was stored at −18° C.

b) Cyclopropylpyridin-2-yl-methylamine hydrochloride: 2.72 g (18.6 mmol) of cyclopropylpyridin-2-yl-methyleneamine (see a) were dissolved in 35 ml of dry methanol. 0.69 g (18.6 mmol) of $NaBH_4$ was added in portions at 0° C. After 30 min at 0° C., the mixture was stirred at room temperature for 2 h, the pH was adjusted to 3 with 1M HCl, the methanol was stripped off in a rotary evaporator, and the residue was freeze dried. 8.8 g of cyclopropylpyridin-2-ylmethylamine hydrochloride mixed with inorganic salts and boric acid were obtained.

Precursor 3 q: Cyclopropylpyridin-3-yl-methylamine hydrochloride

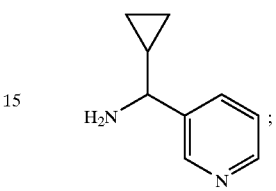

a) Cyclopropylpyridin-3-yl-methyleneamine: 7.5 g (51 mmol) of the imine were isolated as a yellow oil in accordance with the method for precursor 3p from 8.8 g (131 mmol) of cyclopropanecarbonitrile, 25 g (157.5 mmol) of 3-bromopyridine and 173 mmol of n-BuLi solution and after Kugelrohr distillation (130° C./0.2 mbar).

b) Cyclopropylpyridin-3-yl-methylamine hydrochloride: 16.6 g of cyclopropylpyridin-3-ylmethylamine hydrochloride mixed with inorganic salts and boric acid were obtained in accordance with the method for precursor 3p from 7.5 g (51.5 mmol) of imine (see a) and 1.9 g (51.4 mmol) of $NaBH_4$.

Precursor 3 r: 1-(5-Methyl-furan-2-yl)-propylamine

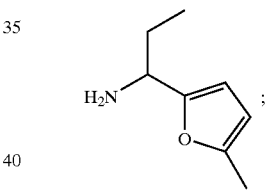

11.35 g (180 mmol) of sodium cyanoborohydride were introduced in portions into 5 g (36 mmol) of 2-methyl-5-propionylfuran and 28.2 g (366 mmol) of ammonium acetate in 300 ml of methanol with stirring, and reaction was allowed to take place at RT for 18 h. The mixture was substantially concentrated and, after addition of 200 ml of dichloromethane, the organic phase was washed 3× with 50 ml of $NaHCO_3$ solution each time, dried over $Na_2SO_4$ and concentrated. 3.9 g (28 mmol) of the amine were obtained in the form of a pale yellow oil.

Precursor 3s: 1-Phenyl-prop-2-ynylamine hydrochloride

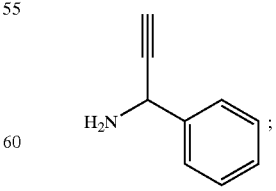

The compound was prepared by a Ritter reaction starting from 1-phenyl-2-propynyl alcohol and subsequent hydrolysis with hydrochloric acid by the method of Bjorn M. Nilsson et al. *J. Heterocycl. Chem.* (1989), 26(2), 269–75.

Precursor 3t: C-Cyclopropyl-C-(6-methoxy-pyridin-2-yl)-methylamine

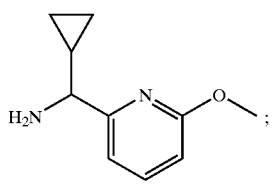

a) Cyclopropanecarbaldehyde O-benzyloxime: 6.7 g (95.6 mmol) of cyclopropanecarbaldehyde were stirred together with 15.3 g (95.6 mmol) of O-benzylhydroxylamine and 15.7 g (191.2 mmol) of sodium acetate in 250 ml of ethanol at room temperature for 18 h and, after concentration, $Na_2SO_4$ was added. The residue was extracted 3× with 50 ml of dichloromethane each time, the organic phase was concentrated, and the crude product was purified by chromatography on silica gel. 5 g (28.6 mmol) of a colorless liquid were obtained.

b) O-Benzyl-N-[cyclopropyl-(6-methoxypyridin-2-yl)-methyl]-hydroxylamine: 8.8 ml (22 mmol) of n-BuLi (2.5 M in toluene) were added to 3.76 g (20 mmol) of 2-bromo-6-methoxypyridine in 20 ml of THF at −78° C. After 30 min, this dark red solution was added to a solution of 1.4 g (8 mmol) of cyclopropanecarbaldehyde O-benzyloxime (see a) and 2.52 ml (20 mmol) of $BF_3$-etherate in 40 ml of toluene, which was stirred at −78° C. for 15 min. The mixture was stirred at −78° C. for 4 h, slowly warmed to RT and, after addition of water, made alkaline with saturated $Na_2CO_3$ solution. The organic phase was separated off, the aqueous phase was extracted with toluene, and the combined organic phases were dried over $Na_2SO_4$ and concentrated. The crude product was taken up in 12 ml of acetonitrile, insoluble constituents were removed, and the product was isolated by preparative HPLC (650 mg, red oil).

c) C-Cyclopropyl-C-(6-methoxy-pyridin-2-yl)-methylamine: 650 mg (2.3 mmol) of O-benzyl-N-[cyclopropyl-(6-methoxypyridin-2-yl)-methyl]-hydroxylamine (see a) were dissolved in 18 ml of glacial acetic acid and diluted with 18 ml of water. 3.3 g of zinc dust were added, and the suspension was reacted in an ultrasonic bath for 24 h. The mixture was filtered through kieselguhr and washed with half-concentrated acetic acid, and the filtrate was partially evaporated and adjusted to pH 11 with saturated $Na_2CO_3$ solution. This was followed by extracting 3× with 100 ml of dichloromethane each time, drying over $Na_2SO_4$ and concentrating. 0.4 g (2.2 mmol) of the product was obtained in the form of a dark red oil.

General method 4 A: Preparation of 2-aminobenzamides from 2-nitrobenzoic acids.

The appropriate 2-nitrobenzoic acid was initially reacted in analogy to general methods 2 and 5 with the particular amine to give a 2-nitrobenzamide. Subsequently, 4 mmol of the 2-nitrobenzamide were hydrogenated in 50 ml of THF and 50 ml of methanol in the presence of a spatula tip of 10% palladium on carbon at RT under atmospheric pressure. The catalyst was filtered off with suction, the reaction mixture was concentrated, and the appropriate 2-aminobenzamide was obtained.

The following precursor was synthesized inter alia in this way:

| Precursor | Structure | Mass |
|---|---|---|
| 4a | 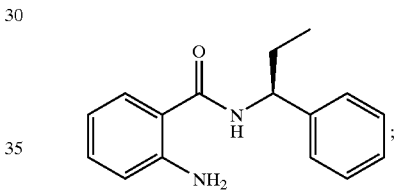 | 318 (M + 1) |

General Method 4 B: Preparation of 2-aminobenzamides from Isatoic Anhydride.

A solution of 20 mmol of isatoic anhydride and 22 mmol of the appropriate amine in 75 ml of DMF was heated at 60° C. until reaction was complete. 100 ml of water were added to the reaction mixture, and the product was filtered off with suction or isolated by extraction.

Precursor 4 b: (S)-2-Amino-N-(1-phenyl-propyl)-benzamide 3.4 g of the title compound were obtained by general method 4 B from 3 g of (S)-1-phenylpropylamine and 3.2 g of isatoic anhydride after 2 h at 60° C.

General Method 5: Reaction of Sulfonylaminobenzoyl Chlorides with Amines.

0.6 mmol of the particular sulfonylaminobenzoyl chloride was added to a solution of 0.66 mmol of the particular amine and 0.9 mmol of triethylamine in 3 ml of methylene chloride, and the mixture was stirred at room temperature overnight. The reaction mixture was diluted with 5 ml of water and 10 ml of methylene chloride, and the organic phase was washed successively with 1 M hydrochloric acid solution and saturated sodium bicarbonate solution. After drying over magnesium sulfate, the solution was concentrated in vacuo, and the product was purified if necessary by preparative HPLC or column chromatography.

General Method 6: Reaction of Sulfonylaminobenzoic Acids with Amines.

0.44 mmol of the particular amine was added dropwise to a solution of 0.42 mmol of the appropriate sulfonylaminobenzoic acid, 0.44 mmol of HOBT and 0.44 mmol of EDAC in 5 ml of THF at 0° C., and the mixture was stirred at RT for 4 to 12 h. The reaction mixture was diluted with EA and washed with dilute hydrochloric acid and sodium bicarbonate solution. Drying over magnesium sulfate and concentration in vacuo result in the appropriate amide which is purified if necessary by preparative HPLC.

General Method 7: Reaction of 2-aminobenzamides with Sulfonyl Chlorides.

A solution of 0.3 mmol of the appropriate sulfonyl chloride in 2 ml of methylene chloride was added dropwise to a solution of 0.2 mmol of the appropriate 2-aminobenzamide (precursor 4) and 0.6 mmol of pyridine in 5 ml of methylene chloride at 0° C., and the mixture was stirred at RT overnight. The organic phase was washed with water, dilute hydrochloric acid and sodium bicarbonate solution, and the resulting crude product was purified if necessary by preparative HPLC.

EXAMPLES

Example 1

(S)-N-(1-Phenyl-propyl)-2-(quinoline-8-sulfonylamino)-benzamide a) 2-(Quinoline-8-sulfonylamino)-benzoic acid: 690 mg of anthranilic acid were added in portions to a solution of 1.32 g of $Na_2CO_3$ in 10 ml of water at 60° C. After stirring at this temperature for 10 minutes, 1.25 g of 8-quinolinesulfonyl chloride were added in portions at 70° C. After stirring at 70° C. for 5 hours, a further 230 mg of 8-quinolinesulfonyl chloride were added. After stirring at 70° C. for 2 hours, the reaction mixture was allowed to cool to RT. The pH was adjusted to 1 with a 2N aqueous HCl solution, and the suspension was stirred at RT for a further hour. The precipitate was then filtered off and dried under medium vacuum at 60° C. to result in 1.57 g of a colorless amorphous solid. MS (ESI): 329 (M+H)$^+$

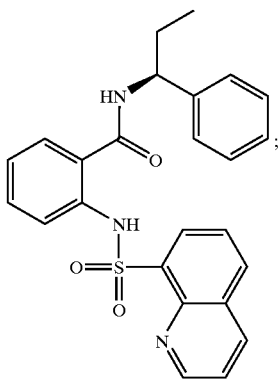

b) 2-(Quinoline-8-sulfonylamino)-benzoyl chloride: 100 mg of 2-(quinoline-8-sulfonylamino)-benzoic acid were dissolved in 1 ml of $SOCl_2$ and boiled under reflux for 4½ hours. The volatile constituents were subsequently removed in vacuo, the residue was taken up in 10 ml of toluene and subsequently the volatile constituents were again removed in vacuo. 120 mg of the acid chloride were obtained and were reacted further without purification.

c) (S)-N-(1-Phenylpropyl)-2-(quinoline-8-sulfonylamino)-benzamide: 120 mg of 2-(quinoline-8-sulfonylamino)-benzoyl chloride were suspended in 4 ml of $CH_2Cl_2$ and, at RT, 85 µl of triethylamine were added. A solution of 41 mg of (S)-1-phenylpropylamine in 2 ml of $CH_2Cl_2$ was then added, and the mixture was stirred at RT for 18 hours. The reaction mixture was diluted with 50 ml of $CH_2Cl_2$ and washed twice with 20 ml of a saturated aqueous $Na_2CO_3$ solution each time. The aqueous phase was then extracted with a further 20 ml of $CH_2Cl_2$, the combined organic phases were dried over $Na_2SO_4$, and the solvent was removed in vacuo. Chromatography of the residue on silica gel with MTB/DIP 1:1 afforded 77 mg of an amorphous solid. $R_f$(MTB/DIP 1:1)=0.31. MS (ES): 446 (M+H)$^+$ The title compounds of examples 2–11 were synthesized in analogy to example 1:

Example 2

(R)-N-(1-Phenylpropyl)-2-(quinoline-8-sulfonylamino)-benzamide

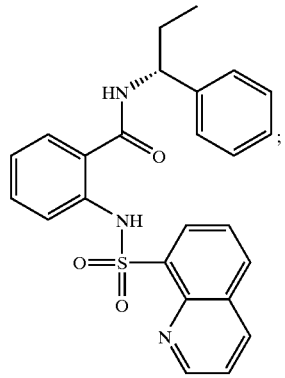

$R_f$(MTB/DIP 1:1)=0.31. MS (ES): 446 (M+H)$^+$

Example 3

(R)-N-(1-Phenylethyl)-2-(quinoline-8-sulfonylamino)-benzamide

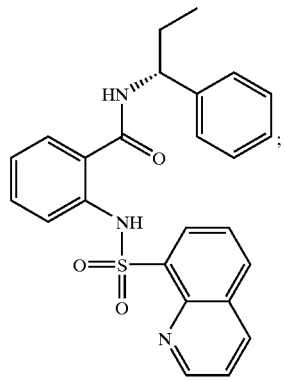

$R_f$(MTB/DIP 1:1)=0.25. MS (ES): 432 (M+H)$^+$

Example 4

(S)-N-(1-Phenylethyl)-2-(quinoline-8-sulfonylamino)-benzamide

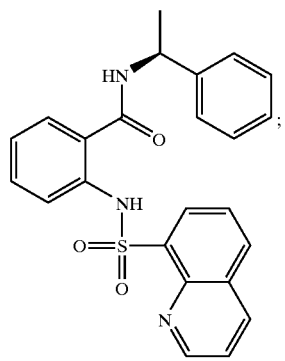

$R_f$(MTB/DIP 1:1)=0.25. MS (ES): 432 (M+H)$^+$

Example 5

(S)-N-[1-(4-Chlorophenyl)-ethyl]-2-(quinoline-8-sulfonylamino)-benzamide

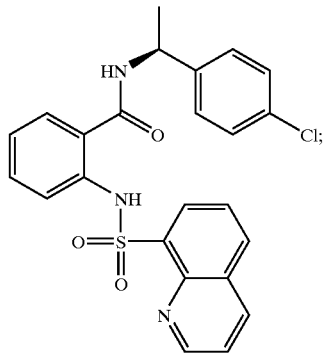

$R_f$(MTB/DIP 1:1)=0.23. MS (ES): 466 (M+H)$^+$

Example 6

(R)-N-[1-(4-Chlorophenyl)-ethyl]-2-(quinoline-8-sulfonylamino)-benzamide

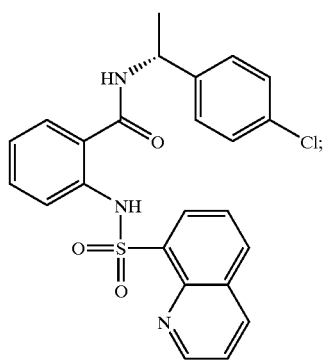

$R_f$(MTB/DIP 1:1) 0.23. MS (ES): 466 (M+H)$^+$

Example 7

4-Chloro-N-pyrazin-2-ylmethyl-2-(quinoline-8-sulfonylamino)-benzamide

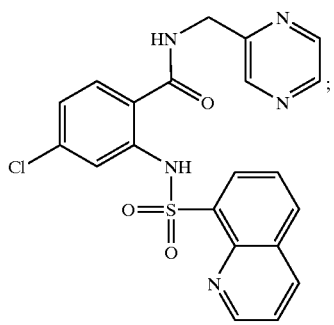

$R_f$(EA)=0.10 MS (ES): 454 (M+H)$^+$

Example 8

N-(2-Benzyloxyethyl)-5-fluoro-2-(quinoline-8-sulfonylamino)-benzamide

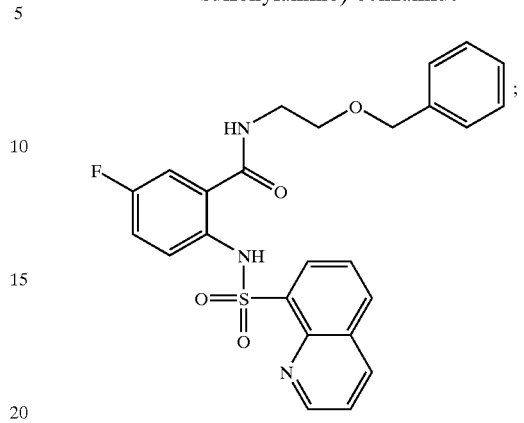

$R_f$(MTB/DIP 1:1)=0.24. MS (ES): 480 (M+H)$^+$

Example 9

N-(2-Benzyloxyethyl)-2-(quinoline-8-sulfonylamino)-benzamide

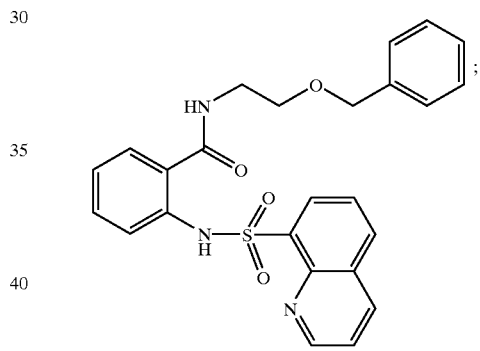

$R_f$(MTB)=0.36. MS (ES): 462 (M+H)$^+$

Example 10

N-(2-Benzyloxyethyl)-5-methoxy-2-(quinoline-8-sulfonylamino)-benzamide

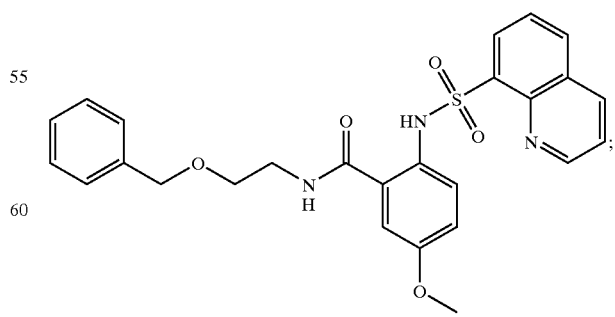

MS (ES): 492 (M+H)$^+$

Example 11

5-Fluoro-N-(2-phenoxyethyl)-2-(quinoline-8-sulfonylamino)-benzamide

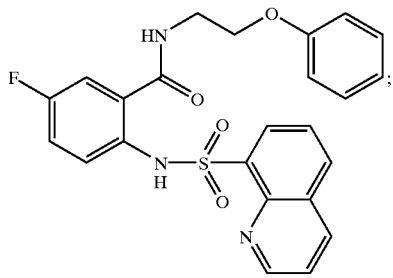

$R_f$(MTB/DIP 1:1)=0.29. MS (ES): 466 (M+H)$^+$

Example 12

N-Benzyl-5-methoxy-N-(1-methyl-1H-imidazol-2-ylmethyl)-2-(quinoline-8-sulfonylamino)-benzamide

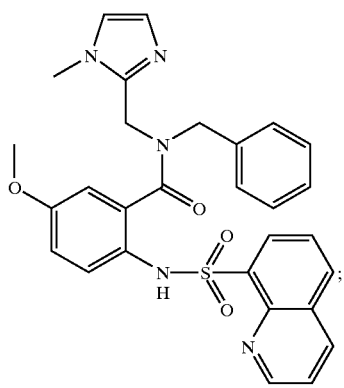

a) Benzyl-(1-methyl-1H-imidazol-2-ylmethyl)-amine: 19.4 g (0.18 mol) of benzylamine were dissolved in 200 ml of methanol and, after addition of 10 g (0.09 mol) of 2-formyl-1-methylimidazole, 11.4 g of sodium cyanoborohydride (0.18 mol) and 10.9 g (0.18 mol) of glacial acetic acid, stirred at RT for 16 h. The solution was concentrated, taken up in EA and washed twice with NaHCO$_3$ solution. The organic phase was dried, concentrated and distilled under medium vacuum to remove benzylamine which was still present. The residue was dissolved in diethyl ether/THF 1:1, and a saturated solution of HCl in diethyl ether was added. The precipitated hydrochloride (20.5 g) was filtered off with suction, washed with diethyl ether and dried in vacuo. MS (ES): 202 (M+H)$^+$ b) N-Benzyl-5-methoxy-N-(1-methyl-1H-imidazol-2-ylmethyl)-2-(quinoline-8-sulfonylamino)-benzamide: 66 mg of benzyl-(1-methyl-1H-imidazol-2-ylmethyl)-amine were reacted as described under 1c) to result in 78 mg of the title compound as an amorphous solid. $R_f$(EA)=0.09. MS (ES): 542 (M+H)$^+$

Example 13

N-(Phenylpyridin-3-ylmethyl)-2-(quinoline-8-sulfonylamino)-benzamide

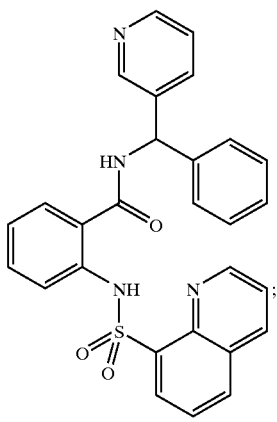

120 mg of phenylpyridin-3-ylmethylamine (Synthesis 1976, 593) were reacted with 450 mg of 2-(quinoline-8-sulfonylamino)-benzoyl chloride in analogy to example 1 which resulted in 130 mg of an amorphous solid. $R_f$(EA)= 0.29. MS (ES): 495 (M+H)$^+$

Example 14

N-Benzyl-N-pyridin-3-ylmethyl-2-(quinoline-8-sulfonylamino)-benzamide

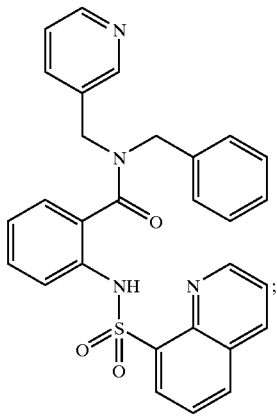

99 mg of N-benzyl-N-(3-pyridylmethyl)amine (precursor 3b) were reacted with 87 mg of 2-(quinoline-8-sulfonylamino)-benzoyl chloride in analogy to example 1 which resulted in 66 mg of an amorphous white solid. MS (ES): 509 (M+H)$^+$

Example 15

N-Cyclohexyl-2-(quinoline-8-sulfonylamino)-benzamide

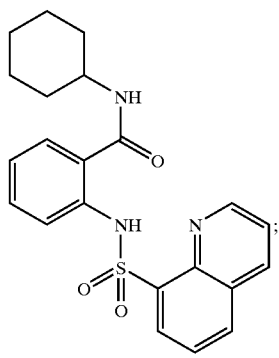

50 mg of cyclohexylamine were reacted with 87 mg of 2-(quinoline-8-sulfonylamino)-benzoyl chloride in analogy to example 1 which resulted in 59 mg of an amorphous white solid. MS (ES): 410 (M+H)$^+$ The title compounds of examples 16–44 were synthesized in analogy to example 1:

Example 16

N-(1-Benzylpropyl)-2-(quinoline-8-sulfonylamino)-benzamide

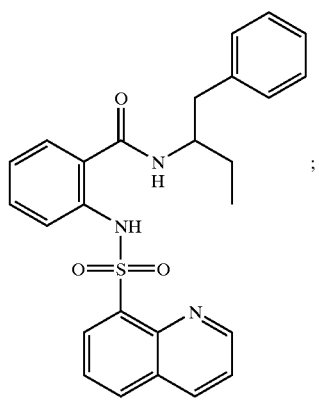

The title compound was obtained from 2-(quinoline-8-sulfonylamino)-benzoyl chloride (example 1b) and 1-benzylpropylamine (precursor 3l). MS (ES): 460 (M+H)$^+$

Example 17

(S)-5-Chloro-2-(5-chlorothiophene-2-sulfonylamino)-N-(1-phenylpropyl)-benzamide

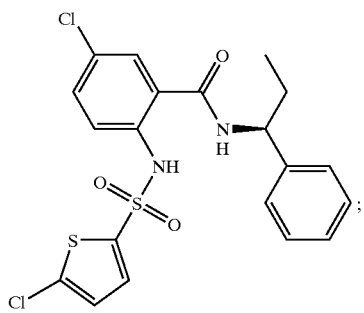

MS (ES): 469 (M+H)$^+$

Example 18

N-(1-Pyridin-3-yl-propyl)-2-(quinoline-8-sulfonylamino)-benzamide

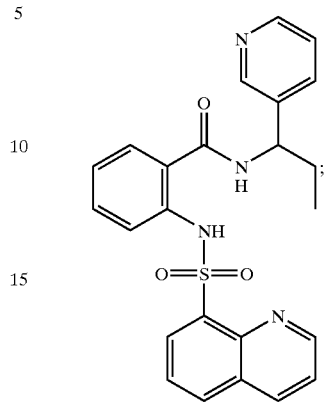

The title compound was obtained from 2-(quinoline-8-sulfonylamino)-benzoyl chloride (example 1b) and 1-pyridin-3-ylpropylamine (precursor 3n). MS (ES): 447 (M+H)$^+$

Example 19

N-Benzyl-N-(1-methyl-1H-imidazol-2-ylmethyl)-2-(quinoline-8-sulfonylamino)-benzamide

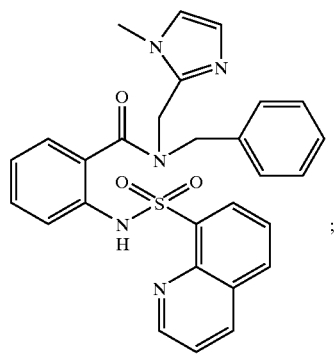

MS (ES): 512 (M+H)$^+$

Example 20

N-Benzyl-N-furan-2-ylmethyl-2-(quinoline-8-sulfonylamino)-benzamide

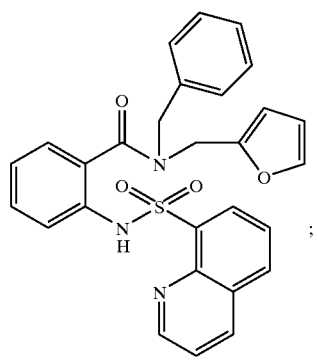

MS (ES): 498 (M+H)$^+$

Example 21

N-Cyclopropyl-N-pyridin-3-ylmethyl-2-(quinoline-8-sulfonylamino)-benzamide

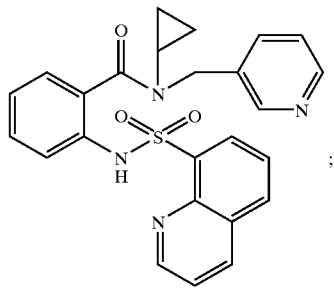

MS (ES) 459 (M+H)$^+$

Example 22

N-Benzyl-N-cyclopropyl-2-(quinoline-8-sulfonylamino)-benzamide

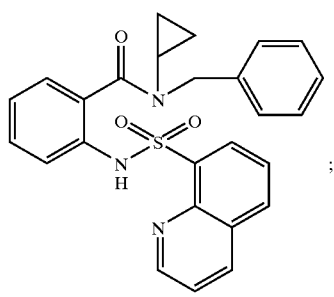

MS (ES): 458 (M+H)$^+$

Example 23

N-Benzyl-N-pyridin-2-ylmethyl-2-(quinoline-8-sulfonylamino)-benzamide

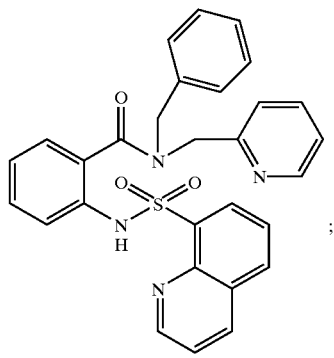

MS (ES): 509 (M+H)$^+$

Example 24

(R)-2-(Quinoline-8-sulfonylamino)-N-(1-p-tolyl-ethyl)-benzamide

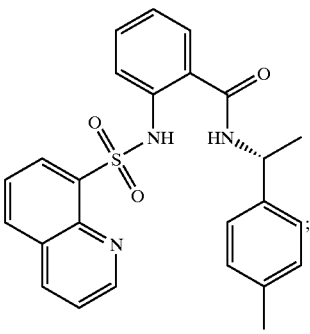

MS (ES): 446 (M+H)$^+$

Example 25

N-[1-(4-Fluorophenyl)-ethyl]-2-(quinoline-8-sulfonylamino)-benzamide

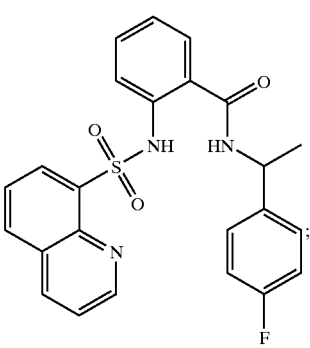

MS (ES): 450 (M+H)$^+$

Example 26

(R)-N-[1-(4-Methoxyphenyl)-ethyl]-2-(quinoline-8-sulfonylamino)-benzamide

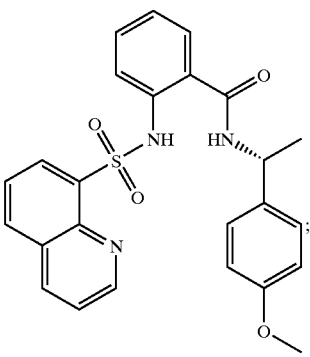

MS (ES): 462 (M+H)$^+$

Example 27

N-(1-Methyl-1-phenylethyl)-2-(quinoline-8-sulfonylamino)-benzamide

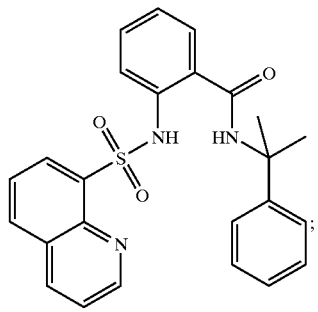

MS (ES): 446 (M+H)$^+$

Example 28

N-Indan-1-yl-2-(quinoline-8-sulfonylamino)-benzamide

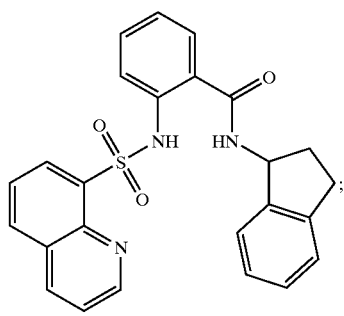

MS (ES): 444 (M+H)$^+$

Example 29

N-[2-(3,4-dihydro-1H-isoquinoline-2-carbonyl)-phenyl]-quinoline-8-sulfonamide

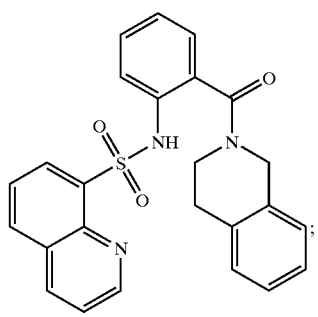

MS (ES): 444 (M+H)$^+$

Example 30

N-[2-(4-Fluorophenyl)-1,1-dimethylethyl]-2-(quinoline-8-sulfonylamino)-benzamide

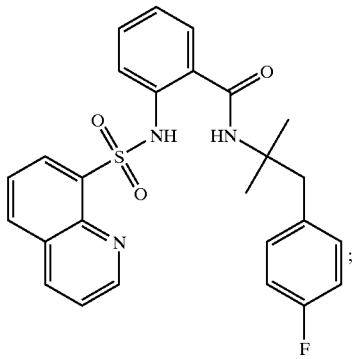

MS (ES): 478 (M+H)$^+$

Example 31

N-(1-Phenylbutyl)-2-(quinoline-8-sulfonylamino)-benzamide

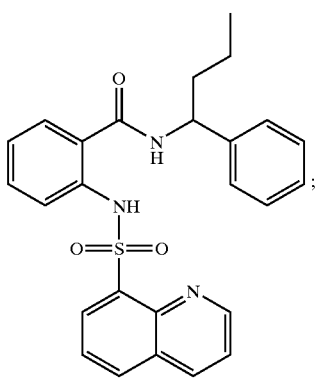

MS (ES): 460 (M+H)$^+$

Example 32

(S)-2-(Quinoline-8-sulfonylamino)-N-(1-p-tolylethyl)-benzamide

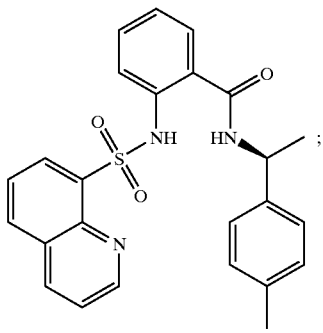

MS (ES): 446 (M+H)$^+$

Example 33

(S)-N-[1-(4-Methoxyphenyl)-ethyl]-2-(quinoline-8-sulfonylamino)-benzamide

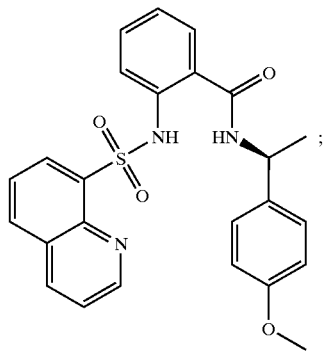

MS (ES): 462 (M+H)+

Example 34

(S)-N-[1-(3-Methoxyphenyl)-ethyl]-2-(quinoline-8-sulfonylamino)-benzamide

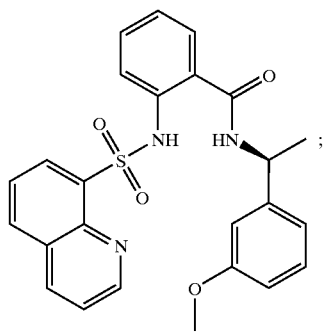

MS (ES): 462 (M+H)+

Example 35

(R)-N-(2-Hydroxy-1-phenylethyl)-2-(quinoline-8-sulfonylamino)-benzamide

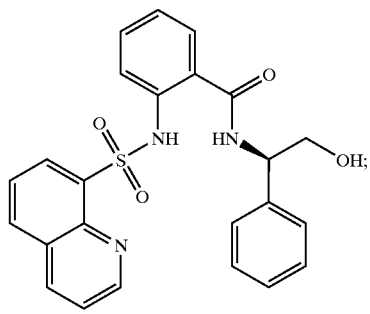

MS (ES): 448 (M+H)+

Example 36

(S)-N-(1-Cyclohexylethyl)-2-(quinoline-8-sulfonylamino)-benzamide

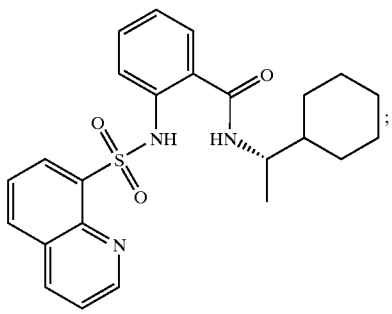

MS (ES): 438 (M+H)+

Example 37

N-(2-Phenylcyclopropyl)-2-(quinoline-8-sulfonylamino)-benzamide

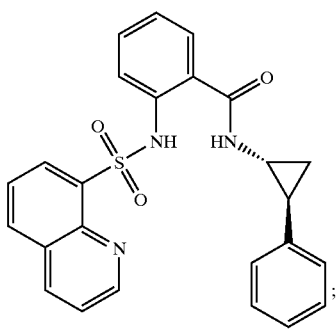

MS (ES): 444 (M+H)+

Example 38

N-[1-(2-Fluorophenyl)-propyl]-2-(quinoline-8-sulfonylamino)-benzamide

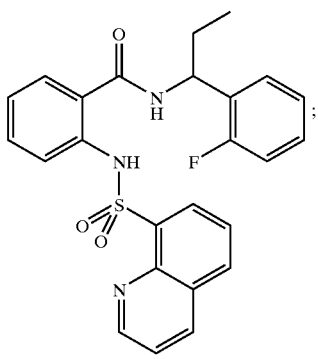

MS (ES): 464 (M+H)+

Example 39

N-(2-Methoxy-1-phenylethyl)-2-(quinoline-8-sulfonylamino)-benzamide

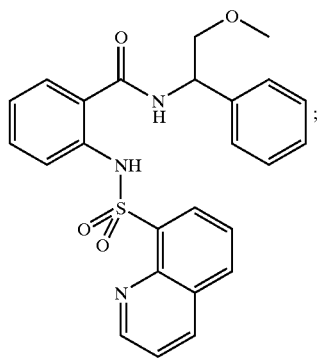

MS (ES): 464 (M+H)+

Example 40

N-[1-(4-Chlorophenyl)-propyl]-2-(quinoline-8-sulfonylamino)-benzamide

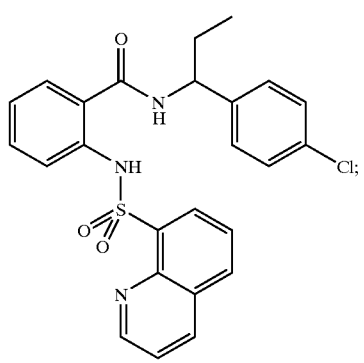

MS (ES): 480 (M+H)+

Example 41

N-Cyclopropyl-N-phenyl-2-(quinoline-8-sulfonylamino)-benzamide

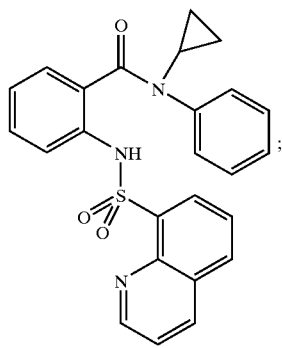

MS (ES): 444 (M+H)+

Example 42

N-(2-Isopropyl-5-methylcyclohexyl)-2-(quinoline-8-sulfonylamino)-benzamide

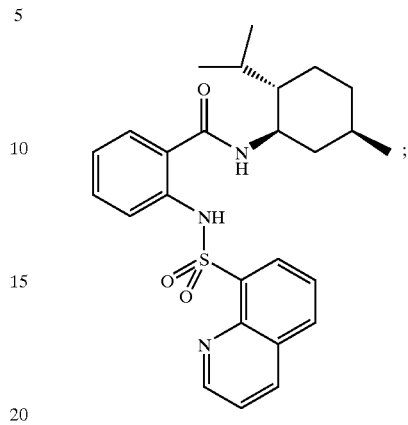

MS (ES): 466 (M+H)+

Example 43

N-(Cyclopropylphenylmethyl)-2-(quinoline-8-sulfonylamino)-benzamide

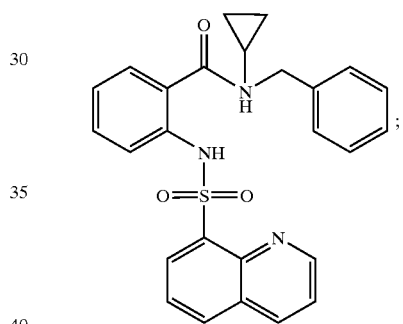

MS (ES): 458 (M+H)+

Example 44

N-[1-(4-Fluorophenyl)-propyl]-2-(quinoline-8-sulfonylamino)-benzamide

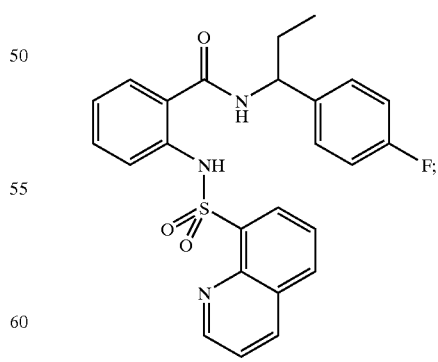

MS (ES): 464 (M+H)+

The title compounds of examples 45–51 were prepared from (S)-2-amino-N-(1-phenylpropyl)-benzamide (precursor 4b) by general method 7:

Example 45

(S)-N-(1-Phenylpropyl)-2-(thiophene-2-sulfonylamino)-benzamide

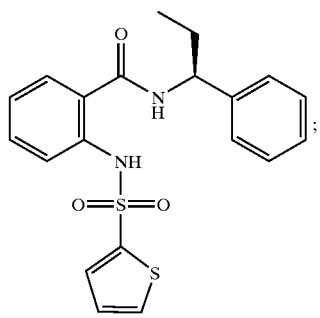

MS (ES): 401 (M+H)+

Example 46

2-(3,5-Dimethylisoxazole-4-sulfonylamino)-N-(1-phenylpropyl)-benzamide

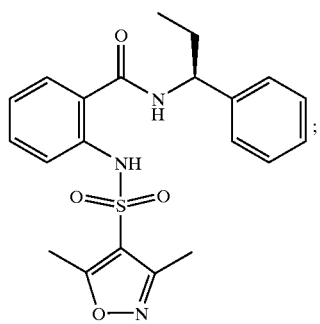

MS (ES): 414 (M+H)+

Example 47

(S)-2-(Isoquinoline-5-sulfonylamino)-N-(1-phenylpropyl)-benzamide

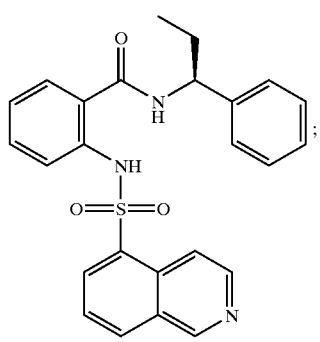

MS (ES): 446 (M+H)+

Example 48

2-(Benzo[1,2,5]oxadiazole-4-sulfonylamino)-N-(1-phenylpropyl)-benzamide

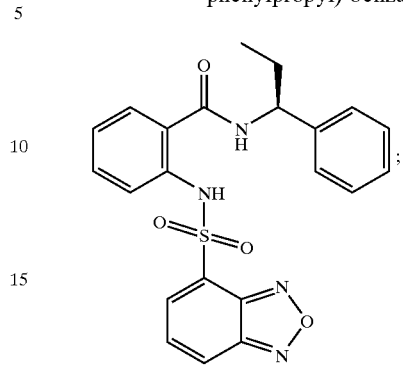

MS (ES): 437 (M+H)+

Example 49

2-(5-Chlorothiophene-2-sulfonylamino)-N-(1-phenylpropyl)-benzamide

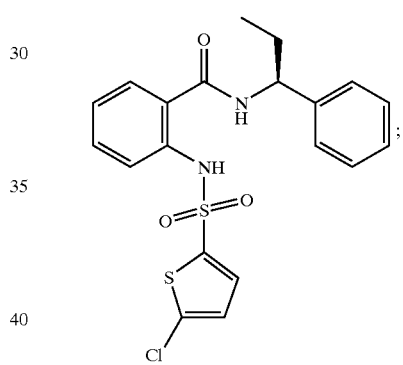

MS (ES): 435 (M+H)+

Example 50

2-(2-Methylquinoline-8-sulfonylamino)-N-(1-phenylpropyl)-benzamide

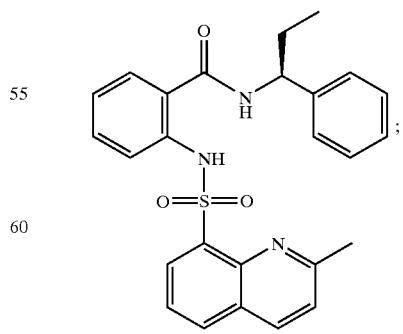

MS (ES): 460 (M+H)+

Example 51

(S)-2-(4-Chloroquinoline-8-sulfonylamino)-N-(1-phenylpropyl)-benzamide

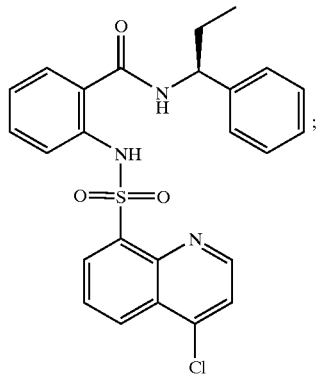

MS (ES): 480 (M+H)+

Example 52

(S)-5-Fluoro-2-(quinoline-8-sulfonylamino)-N-(1-phenylpropyl)-benzamide

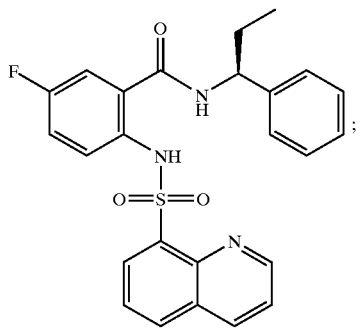

a) 5-Fluoro-2-(quinoline-8-sulfonylamino)-benzoic acid: A reaction mixture composed of 10.0 g (64 mmol) of 5-fluoro-2-aminobenzoic acid, 16.3 g (193 mmol) of sodium bicarbonate and 16.3 g of 8-quinolinesulfonyl chloride in 325 ml of water and 325 ml of ethyl acetate was stirred at RT overnight. The aqueous phase was separated off and extracted once with 50 ml of ethyl acetate. The aqueous phase was then acidified with concentrated hydrochloric acid and stirred for 2 h. The precipitate was filtered off with suction and dried in vacuo to result in 19.5 g of 5-fluoro-2-(quinoline-8-sulfonylamino)-benzoic acid.

b) 5-Fluoro-2-(quinoline-8-sulfonylamino)-N-(1-phenylpropyl)-benzamide: 5.7 g of the title compound were obtained from 5.5 g (15.9 mmol) of 5-fluoro-2-(quinoline-8-sulfonylamino)-benzoic acid and 2.3 g (16.7 mmol) of (S)-phenylpropylamine by general method 6. M.p.: 163° C.; MS (ES): 464 (M+H)+

(S)-5-Fluoro-2-(quinoline-8-sulfonylamino)-N-(1-phenylpropyl)-benzamide sodium salt. 2 ml of a 30 percent strength sodium methanolate solution were added to a solution of 5 g of the compound of example 52 in 120 ml of ethyl acetate. The precipitated sodium salt was filtered off with suction and recrystallized from 25 ml of ethanol to result in 3.3 g of the title compound.

The title compounds of examples 53–58 were prepared from the corresponding precursors 1 and (S)-phenylpropylamine by general method 6:

Example 53

(S)-5-Methoxy-2-(quinoline-8-sulfonylamino)-N-(1-phenylpropyl)-benzamide

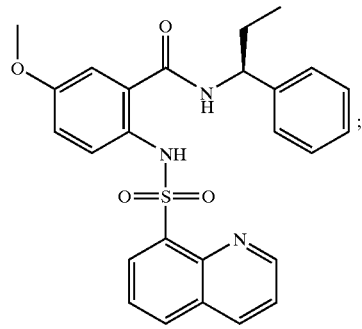

MS (ES): 476 (M+H)+

Example 54

(S)-4-Fluoro-2-(quinoline-8-sulfonylamino)-N-(1-phenylpropyl)-benzamide

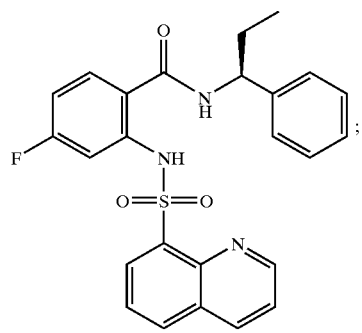

MS (ES): 464 (M+H)+

Example 55

(S)-6-Chloro-2-(quinoline-8-sulfonylamino)-N-(1-phenylpropyl)-benzamide

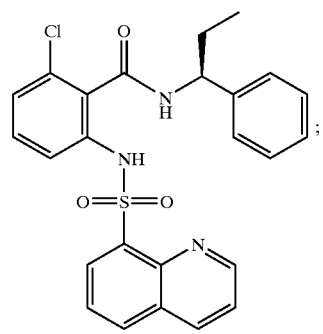

MS (ES): 480 (M+H)+

Example 56

(S)-6-Fluoro-2-(quinoline-8-sulfonylamino)-N-(1-phenylpropyl)-benzamide

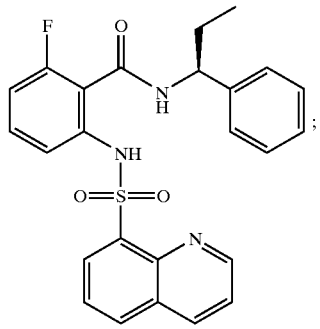

MS (ES): 464 (M+H)+

Example 57

(S)-3-Chloro-2-(quinoline-8-sulfonylamino)-N-(1-phenylpropyl)-benzamide

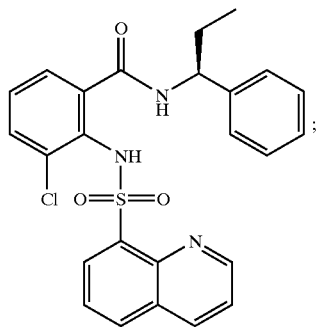

MS (ES): 480 (M+H)+

Example 58

(S)-5-Chloro-2-(quinoline-8-sulfonylamino)-N-(1-phenylpropyl)-benzamide

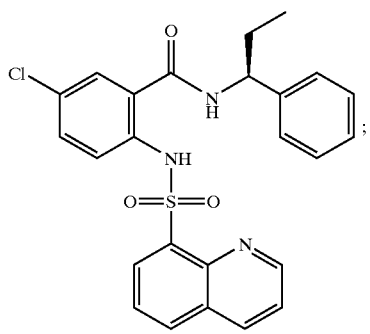

MS (ES): 480 (M+H)+

The title compounds of examples 59–60 were prepared from the corresponding precursors 1 and α-cyclopropylbenzylamine (precursor 3o) by general method 6:

Example 59

N-(Cyclopropylphenylmethyl)-5-fluoro-2-(quinoline-8-sulfonylamino)-benzamide

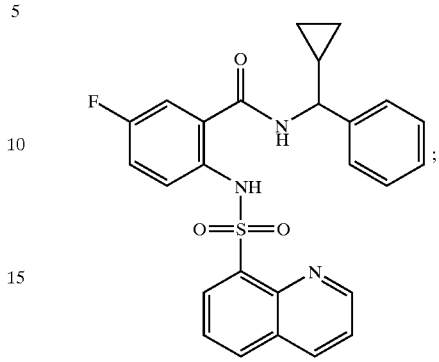

MS (ES): 476 (M+H)+

Example 60

N-(Cyclopropylphenylmethyl)-5-methoxy-2-(quinoline-8-sulfonylamino)-benzamide

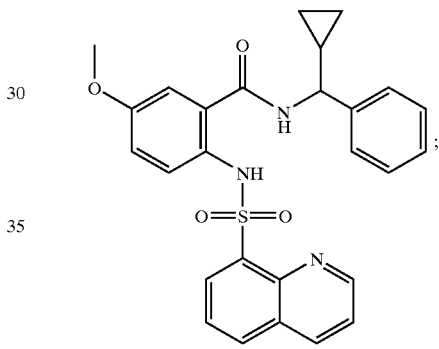

MS (ES) 488 (M+H)+

Example 61

(R)-5-Fluoro-2-(quinoline-8-sulfonylamino)-N-(1-phenylpropyl)-benzamide

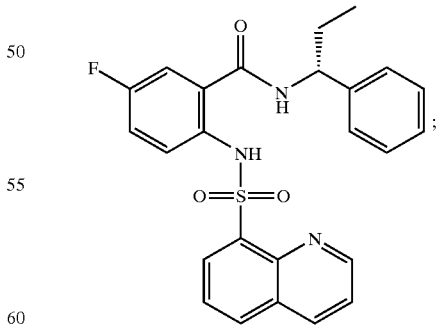

The title compound was obtained in analogy to example 52 from (R)-phenypropylamine MS (ES): 464 (M+H)+

The title compounds of examples 62–63 were prepared from the corresponding precursors 1 and 1-(5-methylfuran-2-yl)-propylamine (precursor 3r) by general method 5:

Example 62

N-[1-(5-Methylfuran-2-yl)-propyl]-2-(quinoline-8-sulfonylamino)-benzamide

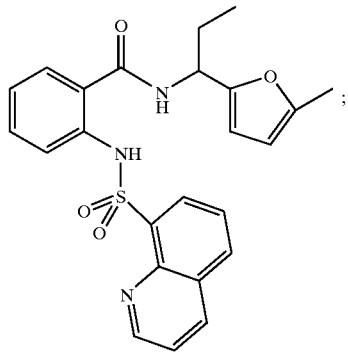

MS (ES): 450 (M+H)+

Example 63

5-Fluoro-N-[1-(5-methylfuran-2-yl)-propyl]-2-(quinoline-8-sulfonylamino)-benzamide

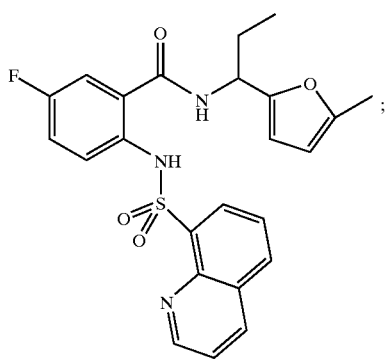

MS (ES): 468 (M+H)+

The title compounds of examples 64–66 were prepared from the corresponding precursors 1 and 1-phenylprop-2-ynylamine (precursor 3s) by general method 5:

Example 64

N-(1-Phenylprop-2-ynyl)-2-(quinoline-8-sulfonylamino)-benzamide

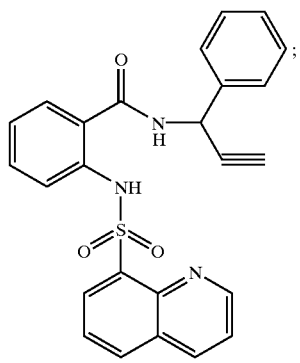

MS (ES): 442 (M+H)+

Example 65

5-Fluoro-N-(1-phenylprop-2-ynyl)-2-(quinoline-8-sulfonylamino)-benzamide

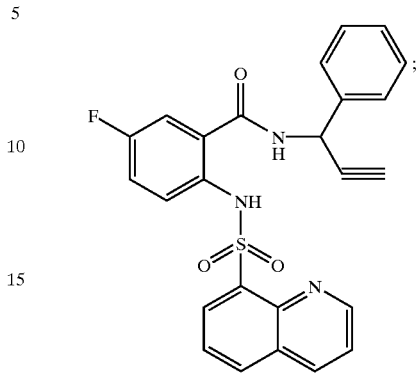

MS (ES): 460 (M+H)+

Example 66

5-Methoxy-N-(1-phenylprop-2-ynyl)-2-(quinoline-8-sulfonylamino)-benzamide

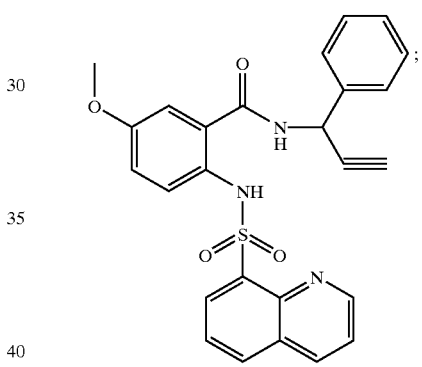

MS (ES): 472 (M+H)+

Example 67

N-(1-Phenylpropyl)-2-(pyridine-2-sulfonylamino)-benzamide

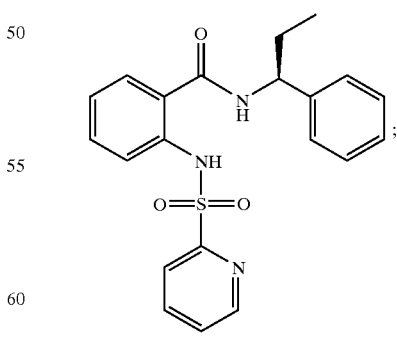

a) Pyridine-2-sulfonyl chloride (analogous to *J. Org. Chem.* 54, 2, 1989, 389–393):

60.4 mmol of 2-mercaptopyridine were dissolved in 100 mL of hydrochloric acid (20%) and cooled to 2–5° C.

Chlorine gas was then passed through the solution for 30 min. in such a way that the temperature did not exceed 5° C. Then a further 50 mL of water were added. The aqueous phase was extracted with ether (3×100 mL), and the organic phase was washed with saturated sodium bicarbonate solution, dried (Na₂SO₄) and concentrated. Yield: 4.52 g (42%).

b) 11 mg of N-(1-phenylpropyl)-2-(pyridine-2-sulfonylamino)-benzamide were obtained as a white solid by general method 7 from 100 mg of (S)-2-amino-N-(1-phenylpropyl)-benzamide and 70 mg of pyridine-2-sulfonyl chloride. MS (ES): 396 (M+H)+

Example 68

5-Methoxy-N-(1-phenylpropyl)-2-(pyridine-2-sulfonylamino)-benzamide

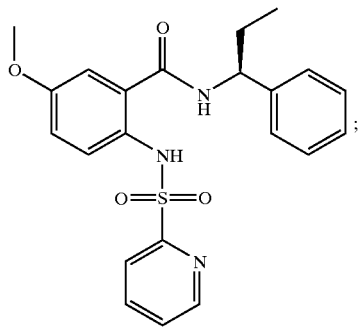

30 mg of the title compound were obtained as a white solid by general method 7 from 100 mg of (S)-2-amino-5-methoxy-N-(1-phenylpropyl)-benzamide and 62 mg of pyridine-2-sulfonyl chloride. MS (ES): 426 (M+H)+

Example 69

5-Methoxy-2-(6-methylpyridine-3-sulfonylamino)-N-(1-phenylpropyl)-benzamide

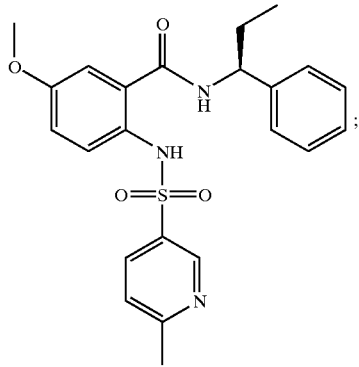

a) 6-Methylpyridine-3-sulfonic acid (analogous to *J. Amer. Chem. Soc.* 65, 1943, 2233–2236): 0.1 mol of 2-picoline was added dropwise over the course of 10 min. to 0.408 mol of oleum (20% free sulfur trioxide) while cooled in ice. Then 0.843 mmol of mercury sulfate was added, and the mixture was stirred at 230° C. for 24 h. The sulfuric acid was then removed by distillation in vacuo. The product was precipitated by adding 200 mL of acetonitrile. It was filtered off with suction, washed with a little acetonitrile and dried at 100° C. Yield: 8.16 g (48%).

b) 6-Methylpyridine-3-sulfonyl chloride (analogous to *J. Org. Chem.* 54, 2, 1989, 389–393).

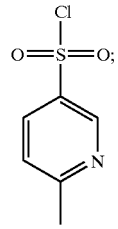

A mixture of 47.1 mmol of 6-methylpyridine-3-sulfonic acid and 56.5 mmol of phosphorus pentachloride was suspended in 80 mL of phosphorus oxychloride and stirred at 120° C. for 24 h. The solution was concentrated in vacuo and, while cooling, water was cautiously added. The aqueous phase was then extracted with ether (3×100 mL), and the organic phase was dried (Na₂SO₄) and concentrated. Yield: 0.6 g (7%).

c) 67 mg of 5-methoxy-2-(6-methylpyridine-3-sulfonylamino)-N-(1-phenylpropyl)-benzamide were obtained as a white solid by general method 7 from 445 mg of (S)-2-amino-5-methoxy-N-(1-phenylpropyl)-benzamide and 300 mg of 6-methyl pyridine-3-sulfonyl chloride. MS (ES): 440 (M+H)+

Example 70

5-Methyl-N-[1-(5-methylfuran-2-yl)-propyl]-2-(pyridine-2-sulfonylamino)-benzamide

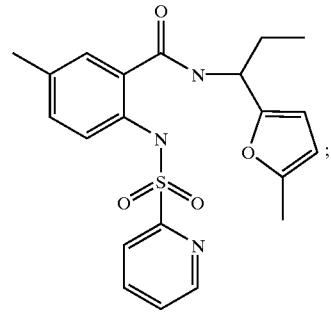

a) 5-Methyl-N-[1-(5-methylfuran-2-yl)-propyl]-2-nitrobenzamide: 2 g (10 mmol) of 2-nitro-5-methylbenzoyl chloride and 1.39 g (10 mmol) of 1-(5-methyl-furan-2-yl)-propylamine (=precursor 3r) were reacted together with 1.3 ml of DIPEA in 20 ml of dichloromethane at room temperature for 18 h. The mixture was diluted with dichloromethane, washed, dried over Na₂SO₄ and purified by chromatography on silica gel. 1.14 g (3.8 mmol) of a pale yellow solid were obtained.

b) 2-Amino-5-methyl-N-[1-(5-methylfuran-2-yl)-propyl]-benzamide: 1.14 g (3.8 mmol) of 5-methyl-N-[1-(5-methylfuran-2-yl)-propyl]-2-nitrobenzamide (see a) were dissolved in 20 ml of methanol and hydrogenated with 1 g of palladium on carbon (10%) under atmospheric pressure at room temperature. Filtration and concentration resulted in 0.9 g (3.3 mmol) of solid.

c) 5-Methyl-N-[1-(5-methylfuran-2-yl)-propyl]-2-(pyridine-2-sulfonylamino)-benzamide: 100 mg (0.37 mmol) of 2-amino-5-methyl-N-[1-(5-methylfuran-2-yl)-propyl]-benzamide (see b) and 117 mg (0.66 mmol) of 2-pyridinesulfonyl chloride hydrochloride were dissolved in 1 ml of pyridine and reacted at room temperature for 18 h. The reaction mixture was concentrated and the compound of example 70 (61 mg, 0.12 mmol) was isolated by means of preparative HPLC as trifluoroacetate after freeze drying.

The following compounds were also obtained in analogy to the examples described above:

| Example | Structure | Mass (ES) |
|---|---|---|
| 71 | 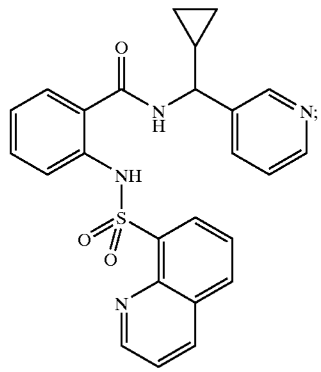 | 459 (M + 1) |
| 72 | 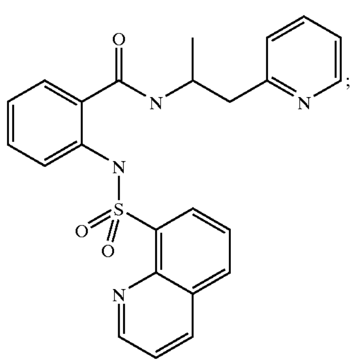 | 447 (M + 1) |
| 73 | 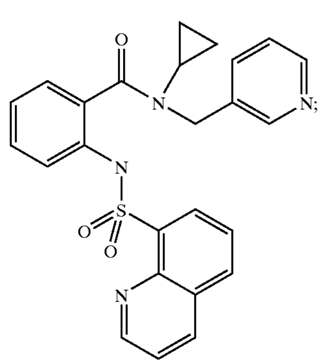 | 459 (M + 1) |

-continued

| Example | Structure | Mass (ES) |
|---|---|---|
| 74 | 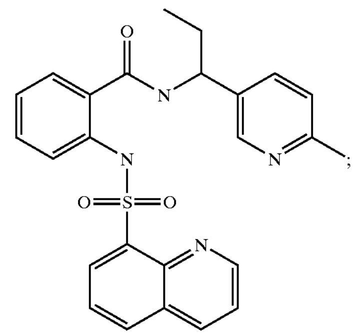 | 461 (M + 1) |
| 75 | 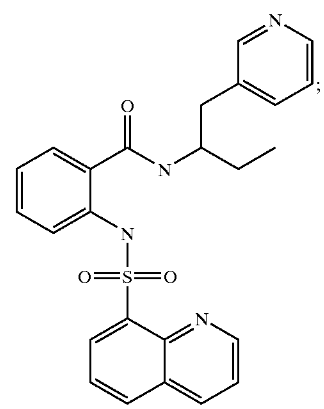 | 461 (M + 1) |
| 76 | 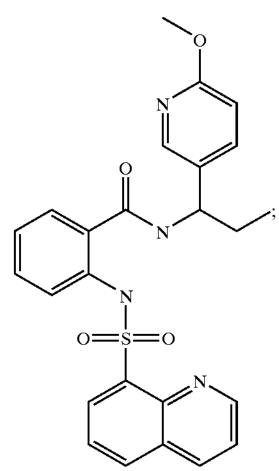 | 477 (M + 1) |

-continued
| Example | Structure | Mass (ES) |
|---|---|---|
| 77 | 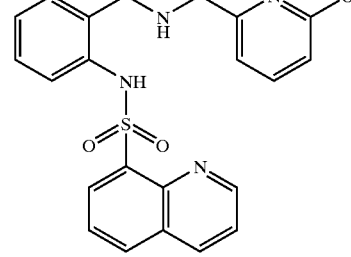 | 499 (M + 1) |
| 78 | 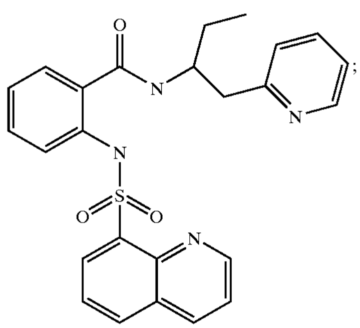 | 461 (M + 1) |
| 79 | 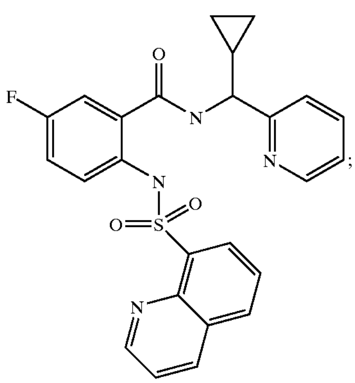 | 477 (M + 1) |
| 80 | 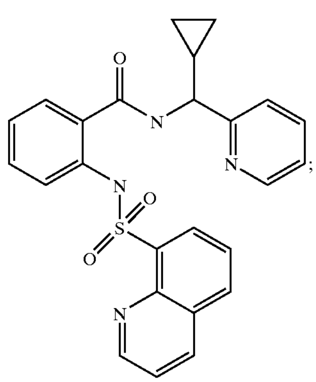 | 459 (M + 1) |
-continued
| Example | Structure | Mass (ES) |
|---|---|---|
| 81 | 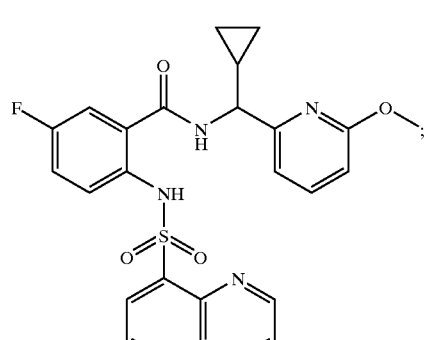 | 489 (M + 1) |
| 82 | 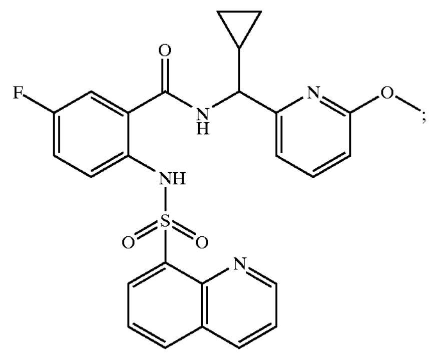 | 507 (M + 1) |
| 83 | 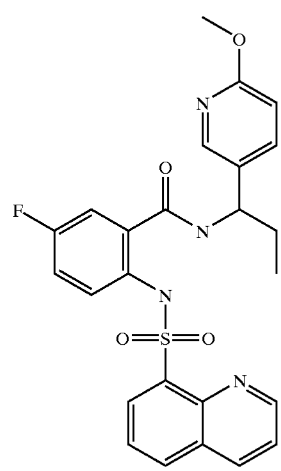 | 495 (M + 1) |
| 84 | 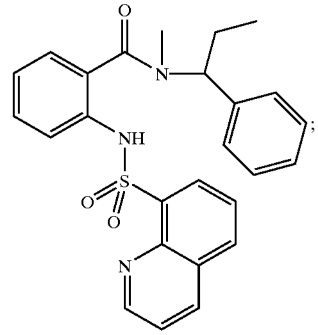 | 460 (M + 1) |

We claim:

1. A compound of formula I in which R1 is:

where A is —$C_nH_{2n}$— and n=0, 1, 2, 3, 4, or 5;
D is a bond or —O—;
E is —$C_mH_{2m}$— and m=0, 1, 2, 3, 4, or 5;
R8 is hydrogen, alkyl having 1, 2, 3, or 4 carbon atoms, or $C_pH_{2p}$—R14 where p is 0, 1, 2, 3, 4, or 5 and where R14 is phenyl, naphthyl, or heteroaryl, where phenyl, naphthyl, or heteroaryl are unsubstituted or substituted by 1, 2, or 3 substituents selected from F, Cl, Br, I, $CF_3$, $OCF_3$, $NO_2$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R9 is hydrogen or alkyl having 1, 2, 3, 4, 5, or 6 carbon atoms;
R10 is hydrogen, alkyl having 1, 2, 3, or 4 carbon atoms, phenyl, naphthyl or heteroaryl, where phenyl, naphthyl, or heteroaryl are unsubstituted or substituted by 1, 2, or 3 substituents selected from F, Cl, Br, I, $CF_3$, $OCF_3$, $NO_2$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R11 is cycloalkyl having 3, 4, 5, or 6 carbon atoms, phenyl, naphthyl, thienyl, furyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl, where phenyl, naphthyl, thienyl, furyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1, 2, or 3 substituents selected from F, Cl, Br, I, $CF_3$, $OCF_3$, $NO_2$, CN, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R12 is alkyl having 1, 2, 3, or 4 carbon atoms, alkynyl having 1, 2, 3, or 4 carbon atoms, cycloalkyl having 3, 4, 5, or 6 carbon atoms, phenyl, naphthyl or heteroaryl where phenyl, naphthyl, or heteroaryl are unsubstituted or substituted by 1, 2, or 3 substituents selected from F, Cl, Br, I, $CF_3$, $OCF_3$, $NO_2$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R13 is $C_pH_{2p}$—R14;
R15 is cycloalkyl having 3, 4, 5, 6, 7, or 8 carbon atoms;
R2 is hydrogen or alkyl having 1, 2, 3, or 4 carbon atoms;
R3 is heteroaryl, where heteroaryl is unsubstituted or substituted by 1, 2, or 3 substituents selected from F, Cl, Br, I, $CF_3$, $OCF_3$, $NO_2$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R4, R5, R6, and R7 are, independently of one another, hydrogen, F, Cl, Br, I, $CF_3$, $OCF_3$, $NO_2$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, or methylsulfonylamino;
and the pharmaceutically acceptable salts thereof.

2. A compound of formula I as claimed in claim 1, in which:
R1 is wherein
A is —$C_nH_{2n}$— and n is 0, 1, 2, or 3;
E is —$C_mH_{2m}$— and m is 0, 1, 2, or 3;
R8 is hydrogen, alkyl having 1, 2, or 3 carbon atoms, or $C_pH_{2p}$—R14 where p is 0, 1, 2, or 3 and where R14 is phenyl, naphthyl or heteroaryl, where phenyl, naphthyl or heteroaryl are unsubstituted or substituted by 1, 2, or 3 substituents selected from F, Cl, $CF_3$, $OCF_3$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R9 is hydrogen or alkyl having 1, 2, 3, or 4 carbon atoms;
R10 is hydrogen, alkyl having 1, 2, or 3 carbon atoms, phenyl, naphthyl or heteroaryl, where phenyl, naphthyl, or heteroaryl are unsubstituted or substituted by 1, 2, or 3 substituents selected from F, Cl, $CF_3$, $OCF_3$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;
R11 is phenyl, naphthyl, thienyl, furyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl where phenyl, naphthyl, thienyl, furyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl are unsubstituted or substituted by 1, 2, or 3 substituents selected from F, Cl, CF₃, OCF₃, CN, COMe, NH₂, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R2 is hydrogen or alkyl having 1, 2, or 3 carbon atoms;

R3 is heteroaryl where heteroaryl is unsubstituted or substituted by 1, 2, or 3 substituents selected from F, Cl, CF₃, OCF₃, CN, COOMe, CONH₂, COMe, NH₂, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R4, R5, R6, and R7 are, independently of one another, hydrogen, F, Cl, CF₃, OCF₃, CN, COMe, OH, alkyl having 1, 2, 3, or 4 carbon atoms, methoxy, ethoxy, dimethylamino, sulfamoyl, methylsulfonyl, or methylsulfonylamino;

and the pharmaceutically acceptable salts thereof.

3. A compound of formula I as claimed in claim 1, in which:
R1 is

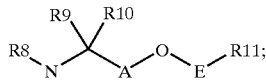

where
A is —$C_nH_{2n}$— and n is 0 or 1;
E is —$C_mH_{2m}$— and m is 0 or 1;
R8 is hydrogen, alkyl having 1, 2, or 3 carbon atoms, or $C_pH_{2p}$—R14 where p is 0 or 1 and where R14 is phenyl, naphthyl, or heteroaryl, where phenyl, naphthyl or heteroaryl are unsubstituted or substituted by 1 or 2 substituents selected from F, Cl, CF₃, OCF₃, CN, COMe, alkyl having 1, 2, 3, or 4 carbon atoms, methoxy, ethoxy, dimethylamino, sulfamoyl, methylsulfonyl, and methylsulfonylamino;
R9 is hydrogen, methyl, or ethyl;
R10 is hydrogen, alkyl having 1, 2, or 3 carbon atoms, phenyl, naphthyl, or heteroaryl, where phenyl, naphthyl, and heteroaryl are unsubstituted or substituted by 1 or 2 substituents selected from F, Cl, CF₃, OCF₃, CN, COMe, alkyl having 1, 2, 3, or 4 carbon atoms, methoxy, ethoxy, dimethylamino, sulfamoyl, methylsulfonyl, and methylsulfonylamino;
R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, CF₃, OCF₃, CN, COMe, alkyl having 1, 2, 3, or 4 carbon atoms, methoxy, ethoxy, dimethylamino, sulfamoyl, methylsulfonyl, and methylsulfonylamino;
R2 is hydrogen, methyl, or ethyl;
R3 is heteroaryl, where heteroaryl is unsubstituted or substituted by 1 or 2 substituents selected from F, Cl, CF₃, OCF₃, CN, COMe, alkyl having 1, 2, 3, or 4 carbon atoms, methoxy, ethoxy, dimethylamino, sulfamoyl, methylsulfonyl, and methylsulfonylamino;
R4, R5, R6, and R7 are, independently of one another, hydrogen, F, Cl, CF₃, OCF₃, CN, COMe, OH, alkyl having 1, 2, 3, or 4 carbon atoms, methoxy, ethoxy, dimethylamino, sulfamoyl, methylsulfonyl, or methylsulfonylamino;

and the pharmaceutically acceptable salts thereof.

4. A compound of formula I as claimed in claim 1, in which
R1 is

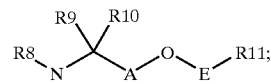

where
A is —$C_nH_{2n}$— and n is 0 or 1;
E is —$C_mH_{2m}$— and m is 0 or 1;
R8 is hydrogen, alkyl having 1, 2, or 3 carbon atoms, or $C_pH_{2p}$—R14 where p is 0 or 1 and where R14 is phenyl, naphthyl, or heteroaryl, where phenyl, naphthyl or heteroaryl are unsubstituted or substituted by 1 or 2 substituents selected from F, Cl, CF₃, OCF₃, CN, COMe, methyl, methoxy, dimethylamino, sulfamoyl, and methylsulfonyl;
R9 is hydrogen, methyl, or ethyl;
R10 is hydrogen, alkyl having 1, 2, or 3 carbon atoms, phenyl, naphthyl, or heteroaryl, where phenyl, naphthyl or heteroaryl are unsubstituted or substituted by 1 or 2 substituents selected from F, Cl, CF₃, OCF₃, CN, COMe, methyl, methoxy, ethoxy, dimethylamino, sulfamoyl, and methylsulfonyl;
R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, CF₃, OCF₃, CN, COMe, methyl, methoxy, ethoxy, dimethylamino, sulfamoyl, and methylsulfonyl;
R2 is hydrogen;
R3 is heteroaryl, where heteroaryl is unsubstituted or substituted by 1 or 2 substituents selected from F, Cl, CF₃, OCF₃, CN, COMe, methyl, methoxy, ethoxy, dimethylamino, sulfamoyl, and methylsulfonyl;
R4 is hydrogen, F, Cl, CF₃, methyl, or methoxy;
R5 is hydrogen, F, Cl, CF₃, methyl, methoxy, COMe, OCF₃, CN, or OH;
R6 is hydrogen, F, Cl, CF₃, methyl, or methoxy;
R7 is hydrogen, F, Cl, CF₃, methyl, ethyl, methoxy, or OH;

and the pharmaceutically acceptable salts thereof.

5. A compound of formula I as claimed in claim 1, in which:
R1 is

where A is —$C_nH_{2n}$— and n is 0, 1, 2, or 3;
D is a bond or —O—;
E is —$C_mH_{2m}$— and m is 0, 1, 2, or 3;
R8 is hydrogen, alkyl having 1, 2, or 3 carbon atoms, or $C_pH_{2p}$—R14 where p is 0, 1, 2, or 3 and where R14 is phenyl, naphthyl, or heteroaryl, where phenyl, naphthyl, or heteroaryl are unsubstituted or substituted by 1, 2, or 3 substituents selected from F, Cl, $CF_3$, $OCF_3$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R9 is hydrogen or alkyl having 1, 2, 3, or 4 carbon atoms;

R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1, 2, or 3 substituents selected from F, Cl, $CF_3$, $OCF_3$, CN, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R12 is alkyl having 1, 2, or 3 carbon atoms, alkynyl having 1, 2, or 3 carbon atoms, cycloalkyl having 3, 4, 5, or 6 carbon atoms, phenyl, naphthyl, or heteroaryl, where phenyl, naphthyl, or heteroaryl are unsubstituted or substituted by 1, 2, or 3 substituents selected from F, Cl, $CF_3$, $OCF_3$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R2 is hydrogen or alkyl having 1, 2, or 3 carbon atoms;

R3 is heteroaryl, where heteroaryl is unsubstituted or substituted by 1, 2, or 3 substituents selected from F, Cl, $CF_3$, $OCF_3$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R4, R5, R6, and R7 are, independently of one another, hydrogen, F, Cl, $CF_3$, $OCF_3$, CN, COMe, OH, alkyl having 1, 2, 3, or 4 carbon atoms, methoxy, ethoxy, dimethylamino, sulfamoyl, methylsulfonyl, or methylsulfonylamino;

and the pharmacologically acceptable salts thereof.

6. A compound of formula I as claimed in claim 1, in which:
R1 is

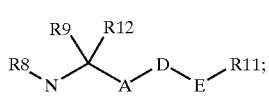

where A is —$C_nH_{2n}$— and n is 0 or 1;
D is a bond or —O—;
E is —$C_mH_{2m}$— and m is 0 or 1;
R8 is hydrogen, alkyl having 1, 2, or 3 carbon atoms, or $C_pH_{2p}$—R14 where p is 0 or 1 and where R14 is phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, alkyl having 1, 2, 3, or 4 carbon atoms, methoxy, ethoxy, dimethylamino, sulfamoyl, methylsulfonyl, and methylsulfonylamino;

R9 is hydrogen, methyl, or ethyl;

R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, $CF_3$, $OCF_3$, CN, COMe, alkyl having 1, 2, 3, or 4 carbon atoms, methoxy, ethoxy, dimethylamino, sulfamoyl, methylsulfonyl, and methylsulfonylamino;

R12 is alkyl having 1, 2, or 3 carbon atoms, ethynyl, cyclopropyl, phenyl, naphthyl, or heteroaryl where phenyl, naphthyl, or heteroaryl are unsubstituted or substituted by 1 or 2 substituents selected from F, Cl, $CF_3$, $OCF_3$, CN, COMe, alkyl having 1, 2, 3, or 4 carbon atoms, methoxy, ethoxy, dimethylamino, sulfamoyl, methylsulfonyl, and methylsulfonylamino;

R2 is hydrogen, methyl, or ethyl;

R3 is heteroaryl, where heteroaryl is unsubstituted or substituted by 1 or 2 substituents selected from F, Cl, $CF_3$, $OCF_3$, CN, COMe, alkyl having 1, 2, 3, or 4 carbon atoms, methoxy, ethoxy, dimethylamino, sulfamoyl, methylsulfonyl, and methylsulfonylamino;

R4, R5, R6, and R7 are, independently of one another, hydrogen, F, Cl, $CF_3$, $OCF_3$, CN, COMe, OH, alkyl having 1, 2, 3, or 4 carbon atoms, methoxy, ethoxy, dimethylamino, sulfamoyl, methylsulfonyl, or methylsulfonylamino;

and the pharmacologically acceptable salts thereof.

7. A compound of formula I as claimed in claim 1 in which:
R1 is

where A is —$C_nH_{2n}$— and n is 0 or 1;
D is a bond or —O—;
E is —$C_mH_{2m}$— and m is 0 or 1;
R8 is hydrogen, alkyl having 1, 2, or 3 carbon atoms, or $C_pH_{2p}$—R14 where p is 0 or 1 and where R14 is phenyl, naphthyl, or heteroaryl, where phenyl, naphthyl or heteroaryl are unsubstituted or substituted by 1 or 2 substituents selected from F, Cl, $CF_3$, $OCF_3$, CN, COMe, methyl, methoxy, ethoxy, dimethylamino, sulfamoyl, methylsulfonyl, and methylsulfonylamino;

R9 is hydrogen, ethyl, or methyl;

R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, $CF_3$, $OCF_3$, CN, COMe, methoxy, ethoxy, dimethylamino, sulfamoyl, and methylsulfonyl;

R12 is alkyl having 1, 2, or 3 carbon atoms, ethynyl, cyclopropyl, phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, ethoxy, dimethylamino, sulfamoyl, methylsulfonyl, and methylsulfonylamino;

R2 is hydrogen;

R3 is heteroaryl, where heteroaryl is unsubstituted or substituted by 1 or 2 substituents selected from F, Cl, CF$_3$, OCF$_3$, CN, COMe, methyl, methoxy, ethoxy, dimethylamino, sulfamoyl, and methylsulfonyl;

R4 is hydrogen, F, Cl, CF$_3$, methyl, or methoxy;

R5 is hydrogen, F, Cl, CF$_3$, methyl, methoxy, COMe, OCF$_3$, CN, or OH;

R6 is hydrogen, F, Cl, CF$_3$, methyl, or methoxy;

R7 is hydrogen, F, Cl, CF$_3$, methyl, methoxy, or OH;

and the pharmacologically acceptable salts thereof.

8. A compound of formula I as claimed in claim 1, in which:

R1 is

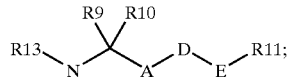

where A is —C$_n$H$_{2n}$— and n=0, 1, 2, or 3;

D is a bond or —O—;

E is —C$_m$H$_{2m}$— and m is 0, 1, 2, or 3;

R9 is hydrogen or alkyl having 1, 2, 3, or 4 carbon atoms;

R10 is hydrogen, alkyl having 1, 2, or 3 carbon atoms, phenyl, naphthyl, or heteroaryl where phenyl, naphthyl, or heteroaryl are unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R11 is phenyl, naphthyl, thienyl, furanyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, thienyl, furanyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl are unsubstituted or substituted by 1, 2, or 3 substituents selected from F, Cl, CF$_3$, OCF$_3$, CN, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R13 is C$_p$H$_{2p}$—R14 where p is 0, 1, 2, or 3 and where R14 is phenyl, naphthyl, or heteroaryl, where phenyl, naphthyl, or heteroaryl are unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R2 is hydrogen or alkyl having 1, 2, or 3 carbon atoms;

R3 is heteroaryl, where heteroaryl is unsubstituted or substituted by 1, 2, or 3 substituents selected from F, Cl, CF$_3$, OCF$_3$, CN, COOMe, CONH$_2$, COMe, NH$_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R4, R5, R6, and R7 are, independently of one another, hydrogen, F, Cl, CF$_3$, OCF$_3$, CN, COMe, OH, alkyl having 1, 2, 3, or 4 carbon atoms, methoxy, ethoxy, dimethylamino, sulfamoyl, methylsulfonyl, or methylsulfonylamino;

and the pharmaceutically acceptable salts thereof.

9. A compound of formula I as claimed in claim 1 in which:

R1 is

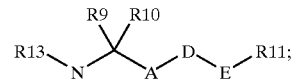

where A is —C$_n$H$_{2n}$— and n is 0 or 1;

D is a bond or —O—;

E is —C$_m$H$_{2m}$— and m is 0 or 1;

R9 is hydrogen, methyl, or ethyl;

R10 is hydrogen, alkyl having 1, 2, or 3 carbon atoms, phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, alkyl having 1, 2, 3, or 4 carbon atoms, NH$_2$, OH, alkyl having 1, 2, 3, or 4 carbon atoms, methoxy, ethoxy, dimethylamino, sulfamoyl, methylsulfonyl, and methylsulfonylamino;

R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R13 is C$_p$H$_{2p}$—R14 where p is 0 or 1 and where R14 is phenyl, naphthyl, or heteroaryl, where phenyl, naphthyl, or heteroaryl are unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R2 is hydrogen, methyl, or ethyl;

R3 is heteroaryl, where heteroaryl is unsubstituted or substituted by 1 or 2 substituents selected from F, Cl, CF$_3$, OCF$_3$, CN, COMe, alkyl having 1, 2, 3, or 4 carbon atoms, methoxy, ethoxy, dimethylamino, sulfamoyl, methylsulfonyl, and methylsulfonylamino;

R4, R5, R6, and R7 are, independently of one another, hydrogen, F, Cl, CF$_3$, OCF$_3$, CN, COMe, OH, alkyl having 1, 2, 3, or 4 carbon atoms, methoxy, ethoxy, dimethylamino, sulfamoyl, methylsulfonyl, or methylsulfonylamino;

and the pharmaceutically acceptable salts thereof.

10. A compound of formula I as claimed in claim 1 in which

R1 is

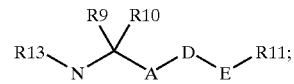

where A is —C$_n$H$_{2n}$— and n is 0 or 1;

D is a bond or —O—;

E is —C$_m$H$_{2m}$— and m is 0 or 1;

R9 is hydrogen, methyl, or ethyl;

R10 is hydrogen, alkyl having 1, 2, or 3 carbon atoms, phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, methyl, methoxy, ethoxy, dimethylamino, sulfamoyl, methylsulfonyl, and methylsulfonylamino;

R11 is phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl, where phenyl, naphthyl, pyridyl, pyrazinyl, pyrimidinyl, pyridazinyl, indolyl, indazolyl, quinolyl, isoquinolyl, phthalazinyl, quinoxalinyl, quinazolinyl, or cinnolinyl are unsubstituted or substituted by 1 or 2 substituents selected from F, Cl, $CF_3$, $OCF_3$, CN, COMe, methyl, methoxy, ethoxy, dimethylamino, sulfamoyl, and methylsulfonyl;

R13 is $C_pH_{2p}$—R14 where p is 0 or 1 and where R14 is phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, methoxy, ethoxy, dimethylamino, sulfamoyl, and methylsulfonyl;

R2 is hydrogen;

R3 is heteroaryl, where heteroaryl is unsubstituted or substituted by 1, 2, or 3 substituents selected from F, Cl, $CF_3$, $OCF_3$, CN, COMe, methoxy, ethoxy, dimethylamino, sulfamoyl, and methylsulfonyl;

R4 is hydrogen, F, Cl, $CF_3$, methyl, or methoxy;

R5 is hydrogen, F, Cl, $CF_3$, methyl, methoxy, COMe, $OCF_3$, CN, or OH;

R6 is hydrogen, F, Cl, $CF_3$, methyl, methoxy, or OH;

R7 is hydrogen, F, Cl, $CF_3$, methyl, ethyl, methoxy, or OH;

and the pharmaceutically acceptable salts thereof.

11. A compound of formula I as claimed in claim 1, in which:

R1 is

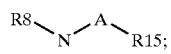

where A is —$C_nH_{2n}$— and n=0, 1, 2, or 3;

R8 is hydrogen, alkyl having 1, 2, or 3 carbon atoms, or $C_pH_{2p}$—R14 where p is 0, 1, 2, or 3 and where R14 is phenyl, naphthyl, or heteroaryl, where phenyl, naphthyl, or heteroaryl are unsubstituted or substituted by 1, 2, or 3 substituents selected from F, Cl, $CF_3$, $OCF_3$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R15 is cycloalkyl having 3, 4, 5, 6, or 7 carbon atoms;

R2 is hydrogen or alkyl having 1, 2, or 3 carbon atoms;

R3 is heteroaryl, where heteroaryl is unsubstituted or substituted by 1, 2, or 3 substituents selected from F, Cl, $CF_3$, $OCF_3$, CN, COOMe, $CONH_2$, COMe, $NH_2$, OH, alkyl having 1, 2, 3, or 4 carbon atoms, alkoxy having 1, 2, 3, or 4 carbon atoms, dimethylamino, sulfamoyl, methylsulfonyl, and methylsulfonylamino;

R4, R5, R6, and R7 are, independently of one another, hydrogen, F, Cl, $CF_3$, $OCF_3$, CN, COMe, OH, alkyl having 1, 2, 3, or 4 carbon atoms, methoxy, ethoxy, dimethylamino, sulfamoyl, methylsulfonyl, or methylsulfonylamino;

and the pharmaceutically acceptable salts thereof.

12. A compound of formula I as claimed in claim 1 in which:

R1 is

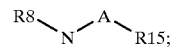

where A is —$C_nH_{2n}$— and n is 0 or 1;

R8 is hydrogen, alkyl having 1, 2, or 3 carbon atoms, or $C_pH_{2p}$—R14 where p is 0 or 1 and where R14 is phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, alkyl having 1, 2, 3, or 4 carbon atoms, methoxy, ethoxy, dimethylamino, sulfamoyl, methylsulfonyl, and methylsulfonylamino;

R15 is cycloalkyl having 3, 4, 5, 6, or 7 carbon atoms;

R2 is hydrogen, methyl, or ethyl;

R3 is heteroaryl, where heteroaryl is unsubstituted or substituted by 1 or 2 substituents selected from F, Cl, $CF_3$, $OCF_3$, CN, COMe, alkyl having 1, 2, 3, or 4 carbon atoms, methoxy, ethoxy, dimethylamino, sulfamoyl, methylsulfonyl, and methylsulfonylamino;

R4, R5, R6, and R7 are, independently of one another, hydrogen, F, Cl, $CF_3$, $OCF_3$, CN, COMe, OH, alkyl having 1, 2, 3, or 4 carbon atoms, methoxy, ethoxy, dimethylamino, sulfamoyl, methylsulfonyl, or methylsulfonylamino;

and the pharmaceutically acceptable salts thereof.

13. A compound of formula I as claimed in claim 1 in which:

R1 is

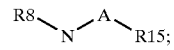

where A is —$C_nH_{2n}$— and n is 0 or 1;

R8 is hydrogen, alkyl having 1, 2, or 3 carbon atoms, or $C_pH_{2p}$—R14 where p is 0 or 1 and where R14 is phenyl, naphthyl, or heteroaryl, where phenyl, naphthyl, or heteroaryl are unsubstituted or substituted by 1 or 2 substituents selected from F, Cl, $CF_3$, $OCF_3$, CN, COMe, methyl, methoxy, ethoxy, dimethylamino, sulfamoyl, and methylsulfonyl;

R15 is cycloalkyl having 3, 4, 5, 6, or 7 carbon atoms;

R2 is hydrogen;

R3 is heteroaryl, where heteroaryl is unsubstituted or substituted by 1 or 2 substituents selected from F, Cl, $CF_3$, $OCF_3$, CN, COMe, methyl, methoxy, ethoxy, dimethylamino, sulfamoyl, or methylsulfonyl;

R4 is hydrogen, F, Cl, $CF_3$, methyl, or methoxy;

R5 is hydrogen, F, Cl, $CF_3$, methyl, methoxy, COMe, $OCF_3$, CN, or OH;

R6 is hydrogen, F, Cl, $CF_3$, methyl, methoxy, or OH;

R7 is hydrogen, F, Cl, $CF_3$, methyl, ethyl, methoxy, or OH;

and the pharmaceutically acceptable salts thereof.

14. A pharmaceutical composition comprising:

one or more compounds of claim 1; and one or more pharmaceutically acceptable carriers or additives.

15. A method of treatment or prevention of K⁺ channel-mediated diseases comprising administering a compound of claim 1 to a subject in need thereof.

16. A method of treatment or prevention of cardiac arrhythmias comprising administering a compound of claim 1 to a subject in need thereof.

17. A method of treatment or prevention of reentry arrhythmias comprising administering a compound of claim 1 to a subject in need thereof.

18. A method of treatment or prevention of supraventricular arrhythmias comprising administering a compound of claim 1 to a subject in need thereof.

19. A method of treatment or prevention of atrial fibrillation or atrial flutter comprising administering a compound of claim 1 to a subject in need thereof.

20. A pharmaceutical composition comprising:

one or more compounds of claim 1; and one or more pharmaceutically acceptable carriers or additives; and a beta-blocker.

* * * * *